US006284522B1

(12) United States Patent
Wackett et al.

(10) Patent No.: US 6,284,522 B1
(45) Date of Patent: Sep. 4, 2001

(54) ISOLATED AND PURIFIED DNA MOLECULE AND PROTEIN FOR THE DEGRADATION OF TRIAZINE COMPOUNDS

(75) Inventors: Lawrence P. Wackett, St. Paul; Michael J. Sadowsky, Roseville; Mervyn L. de Souza, St. Paul, all of MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 08/546,793

(22) Filed: Oct. 23, 1995

(51) Int. Cl.$^7$ ............................... B09B 3/00; C12N 9/14; C07H 21/04

(52) U.S. Cl. .................... 435/262.5; 435/69.1; 435/91.1; 435/91.4; 435/252.3; 435/122; 530/350; 536/24.3

(58) Field of Search ................. 435/69.1, 91.1, 435/91.4, 252.3, 262.5, 122, 195; 530/350; 536/24.3, 23.7, 23.2

(56) References Cited

U.S. PATENT DOCUMENTS

| | | | |
|---|---|---|---|
| 4,745,064 | 5/1988 | Cook et al. | 435/253 |
| 5,429,949 | 7/1995 | Radosevich et al. | 435/252.1 |
| 5,508,193 | 4/1996 | Mandelbaum et al. | 435/25.3 |

FOREIGN PATENT DOCUMENTS

| | | | |
|---|---|---|---|
| 0 141 784 | 10/1984 | (EP) | C02F/3/34 |
| WO 95/01437 | 1/1995 | (WO) | C12N/15/12 |

OTHER PUBLICATIONS de Souza et al., "Atrazine Chlorohydrolase from Pseudomonas sp. Strain ADP: Gene Sequence, Enzyme Purification, and Protein Characterization," *Journal of Bacteriology*, 178(16), 4894–4900 (1996).

EMBL Database entry TT3ITRA, Accession No. M13165, Jul. 16, 1988 Sequence: Huang et al., "Analysis of Tn3 sequences required for transposition and immunity," *Gene*, 41, 23–31 (1986).

Shao et al., "Cloning and Expression of the s–Traizine Hydrolase Gene (trzA) from *Rhodococcus corallinus* and Development of Rhodococcus Recombinant Strains Capable of Dealkylating and Dechlorinating the Herbicide Atrazine," *Journal of Bacteriology*, 177(20), 5748–5755 (1995).

EMBL Database Entry RCTRZA Accession No. L16534; Oct. 2, 1993, Shao et al., *Rhodococcus corallinus* (NRRL 15444B) N–ethylammeline chlorohydrolase (trzA) gene, complete cds.

de Souza et al., "Cloning, Characterization, and Expression of a Gene Region from Pseudomonas sp. Strain ADP Involved in the Dechlorination of Atrazine," *Applied and Environmental Microbiology*, 61(9) 3373–3378 (1995).

U.S. Department of Agriculture—BARD Program, Grant No. 94–34339–112, obtained from the Departartment of BARD (1994) Abstract only.

Armstrong et al., "Adsorption Catalyzed Chemical Hydrolysis of Atrazine," *Environ. Sci. Technol.*, 2(9), 683–689 (1968).

Behki et al., "Metabolism of the Herbicide Atrazine by Rhodococcus Strains," *Applied and Environmental Microbiology*, 59(6), 1955–1959 (1993).

Behki et al., "Degradation of Atrazine by Pseudomonas: N–Dealkylation and Dehalogenation of Atrazine and Its Metabolites," *J. Agric. Food Chem.*, 34, 746–749 (1986).

Bergman et al., "Determination of Trace Amounts in Chlorine in Naphtha," *Anal. Chem.*, 29(2), 241–243 (1957).

Chang et al., "Construction and Characterization of Amplifiable Multicopy DNA Cloning Vehicles Derived from the P15A Cryptic Miniplasmid," *J. Bacteriol.*, 134(3), 1141–1156 (1978).

Cook et al., "s–Triazines as Nitrogen Sources for Bacteria" *J. Agric. Food Chem.*, 29, 1135–1143 (1981).

Cook, "Biodegradation of s–triazine xenobiotics," *FEMS Microbiology Reviews*, 46, 93–116 (1987).

de Bruijn et al., "The use of transposon Tn5 mutagenesis in the rapid generation of correlated physical and genetic maps of DNA segments cloned into multicopy plasmids—a review," *Gene*, 27, 131–149 (1984).

de Souza et al., "Identification of a Gene Cluster from Pseudomonas sp. ADP, Involved in Atrazine Biodegradation," *Abstract of the 95th General Meeting of the American Society for Microbiology*, No. Q–89 (1995).

Eaton et al., "Cloning and Analysis of s–Triazine Catabolic Genes from Pseudomonas sp. Strain NRRLB–12227," *J. Bacteriol.*, 173, 1215–1222 (1991).

Eaton et al., "Cloning and Comparison of the DNA Encoding Ammelide Aminohydrolase and Cyanuric Acid Amidohydrolase from Three s–Triazine–Degrading Bacterial Strains," 173(3), 1363–1366 (1991).

Erickson et al., "Degradation of Atrazine and Related S–Triazines," *Critical Reviews in Environmental Control*, 19, 1–13 (1989).

Giardina et al., "4–Amino–2–Chloro–1,3,5–triazine: A New Metabolite of Atrazine by a Soil Bacterium," *Agric. Biol. Chem.*, 44(9), 2067–2072 (1980).

(List continued on next page.)

Primary Examiner—Rebecca E. Prouty
Assistant Examiner—Richard Hutson
(74) Attorney, Agent, or Firm—Mueting, Raasch & Gebhardt, P.A.

(57) ABSTRACT

An isolated and purified DNA molecule, and an isolated and purified protein, that are involved in the degradation of s-triazine compounds (e.g., atrazine) are provided. A method for the purification of this protein is also provided.

8 Claims, 7 Drawing Sheets

OTHER PUBLICATIONS

Hanahan, *DNA Cloning Vol. II*; D. M. Glover; Ed.; IRL Press Limited: Oxford, England; 109–135 (1985).

Hsiao et al., "High–frequency transformation of yeast by plasmids containing the cloned yeast ARG4 gene," *Proc. Natl. Acad. Sci. USA*, 76(8), 3829–3833 (1979).

Jessee et al., "Anaerobic Degradation of Cyanuric Acid, Cysteine, and Atrazine by a Facultative Anaerobic Bacterium," *Applied and Environmental Mirobiology*, 45(1), 97–102 (1983).

Leong et al., "Heme Biosynthesis in Rhizobium," *J. Bio. Chem.*, 257(15) 8724–8730 (1982).

Maleki et al., "Degradation of Atrazine by Soil Consortia: Characterization of Enzymatically Active Fractions from Cell–Bound and Cell–Free Enrichment Cultures," *Abstracts of the 95th General Meeting of the American Society for Microbiology*, Abstract No. Q–88 (1995).

Mandelbaum et al., "Mineralization of the s–Triazine Ring of Atrazine by Stable Bacterial Mixed Cultures," *Applied and Enviornmental Microbiology*, 59(6), 1695–1701 (1993).

Mandelbaum et al., "Rapid Hydrolysis of Atrazine to Hydroxyatrazine by Soil Bacteria," *Environ. Sci. Technol.*, 27(9) 1943–1946 (1993).

Mandelbaum et al., "Isolation and Characterization of a Pseudomonas sp. That Mineralizes the S–Triazine Herbicide At," *Applied and Environmental Microbiology*, 61(4) 1451–1457 (1995).

Maniatis et al., *Molecular Cloning: A Laboratory Manual*, Cold Springs Harbor Press: Cold Spring Harbor, NY (1989), Bookcover, Copyright Pate, and Table of Table of Contents (pp. v–xxxii).

Maxam et al., "Sequencing End–Labeled DNA with Base–Specific Chemical Cleavages," *Methods in Enzymology*, 65, 499–561 (1980).

Messing et al., "A System for Shotgun DNA Sequencing," *Nucl. Acids Res.*, 9, 309–321 (1981).

Mulbry, "Purification and Characterization of an Inducible s–Triazine Hydrolase from *Rhodococcus corallinus* NRRL B–15444R," *Applied and Environmental Microbiology*, 60(2), 613–618 (1994).

Nagy et al., "A Single Cytochrome P–450 System is Involved in Degradation of the Herbicides EPTC (S–Ethyl Dipropylthiocarbamate) and Atrazine by Rhodococcus sp. Strain NI86/21," *Applied and Environmental Microbiology*, 61(5), 2056–2060 (1995).

Nair et al., "Effect of Two Electron Acceptors on Atrazine Mineralization Rates in Soil," *Environ. Sci. Technol.*, 26, 2298–2300 (1992).

Radosevich et al., "Degration and Mineralization of Atrazine by a Soil Bacterial Isolate," *Applied and Environmental Microbiology*, 61(1), 297–302 (1995).

Sadowsky et al., "Genetic Diversity in *Bradyrhizobium japonicum* Serogroup 123 and Its Relation to Genotype–Specific Nodulation of Soybean," *Applied and Environmental Microbiology*, 53(11), 2624–2630 (1987).

Schmidt et al., "Fluorescent–Antibody Approach to Study of Rhizobia in Soil," *Journal of Bacteriology*, 95(6), 1987–1992 (1968).

Shao et al., "Cloning of the Genes for Degradation of the Herbicides EPTC (S–Ethyl Dipropylthiocarbamate) and Atrazine from Rhodococcus sp. Strain TE1," *Applied and Environmental Microbiology*, 61(5), 2061–2065 (1995).

Shingler et al., "Nucleotide Sequence and Functional Analysis of the Complete Phenol/3,4–Dimethylphenol Catabolic Pathway of Pseudomonas sp. Strain CF600," *Journal of Bacteriology*, 174(3), 711–724 (1992).

Staskawicz et al., "Molecular Characterization of Cloned Avirulence Genes from Race) and Race 1 of *Pseudomonoas syringae* pv. *glycinea*", *Journal of Bacteriology*, 169(12), 5789–5794 (1987).

Stucki et al., "Microbial Atrazine Mineralisation Under Carbon Limited and Denitrifying Conditions," *Wat. Res.*, 29(1), 291–296 (1995).

Van Solingen et al., "Fusion of Yeast Spheroplasts," *Journal of Bacteriology*, 130(2), 946–947 (1977).

Wackett et al., ASM Poster Presentation, May 21–25, 1995.

Yanze–Kontchou et al., "Mineralization of the Herbicide Atrazine as a Carbon Source by a Pseudomonas Strain," *Applied and Environmental Microbiology*, 60(12), 4297–4302 (1994).

Fig. 2

Fig. 6

```
   1 CTCGGGTAAC TTCTTGAGCG CGGCCACAGC AGCCTTGATC ATGAAGGCGA
  51 GCATGGTGAC CTTGACGCCG CTCTTTTCGT TCTCTTTGTT GAACTGCACG
 101 CGAAAGGCTT CCAGGTCGGT GATGTCCGCG TCGTCGTGGT TGGTGACGTG
 151 CGGGATGACC ACCCAGTTGC GGTGCAGGTT TTTCGATGGC ATAATATCTG
                                                 atzA →
 201 CGTTGCGACG TGTAACACAC TATTGGAGAC ATATCATGCA AACGCTCAGC
 251 ATCCAGCACG GTACCCTCGT CACGATGGAT CAGTACCGCA GAGTCCTTGG
 301 GGATAGCTGG GTTCACGTGC AGGATGGACG GATCGTCGCG CTCGGAGTGC
 351 ACGCCGAGTC GGTGCCTCCG CCAGCGGATC GGGTGATCGA TGCACGCGGC
 401 AAGGTCGTGT TACCCGGTTT CATCAATGCC CACACCCATG TGAACCAGAT
 451 CCTCCTGCGC GGAGGGCCCT CGCACGGACG TCAATTCTAT GACTGGCTGT
 501 TCAACGTTGT GTATCCGGGA CAAAAGGCGA TGAGACCGGA GGACGTAGCG
 551 GTGGCGGTGA GGTTGTATTG TGCGGAAGCT GTGCGCAGCG GGATTACGAC
 601 GATCAACGAA AACGCCGATT CGGCCATCTA CCCAGGCAAC ATCGAGGCCG
 651 CGATGGCGGT CTATGGTGAG GTGGGTGTGA GGGTCGTCTA CGCCCGCATG
 701 TTCTTTGATC GGATGGACGG GCGCATTCAA GGGTATGTGG ACGCCTTGAA
 751 GGCTCGCTCT CCCCAAGTCG AACTGTGCTC GATCATGGAG GAAACGGCTG
 801 TGGCCAAAGA TCGGATCACA GCCCTGTCAG ATCAGTATCA TGGCACGGCA
 851 GGAGGTCGTA TATCAGTTTG GCCCGCTCCT GCCACTACCA CGGCGGTGAC
 901 AGTTGAAGGA ATGCGATGGG CACAAGCCTT CGCCCGTGAT CGGGCGGTAA
 951 TGTGGACGCT TCACATGGCG GAGAGCGATC ATGATGAGCG GATTCATGGG
1001 ATGAGTCCCG CCGAGTACAT GGAGTGTTAC GGACTCTTGG ATGAGCGTCT
1051 GCAGGTCGCG CATTGCGTGT ACTTTGACCG GAAGGATGTT CGGCTGCTGC
1101 ACCGCCACAA TGTGAAGGTC GCGTCGCAGG TTGTGAGCAA TGCCTACCTC
1151 GGCTCAGGGG TGGCCCCCGT GCCAGAGATG GTGGAGCGCG GCATGGCCGT
1201 GGGCATTGGA ACAGATAACG GAATAGTAA TGACTCCGCA AACATGATCG
1251 GAGACATGAA GTTTATGGCC CATATTCACC GCGCGGTGCA TCGGGATGCG
1301 GACGTGCTGA CCCCAGAGAA GATTCTTGAA ATGGCGACGA TCGATGGGGC
1351 GCGTTCGTTG GGAATGGACC ACGAGATTGG TTCCATCGAA ACCGGCAAGC
1401 GCGCGGACCT TATCCTGCTT GACCTGCGTC ACCTCAGACG ACTCTCACAT
1451 CATTTGGCGG CCACGATCGT GTTTCAGGCT TACGGCAATG AGGTGGACAC
1501 TGTCCTGATT GACGGAAACG TTGTGATGGA AACCGCCGC TTGAGCTTTC
1551 TTCCCCCTGA ACGTGAGTTG GCGTTCCTTG AGGAAGCGCA GAGCCGCGCC
1601 ACAGCTATTT TGCAGCGGGC GAACATGGTG GCTAACCCAG CTTGGCGCAG
1651 CCTCTAGGAA ATGACGCCGT TGCTGCATCC GCCGCCCCTT GAGGAAATCG
1701 CTGCCATCTT GGCGCGGCTC GGATTGGGGG GCGGACATGA CCTTGATGGA
1751 TACAGAATTG CCATGAATGC GGCACTTCCG TCCTTCGCTC GTGTGGAATC
1801 GTTGGTAGGT GAGGGTCGAC TGCGGGCGCC AGCTTCCCGA AGAGGTGAAA
1851 GGCCCGAG
```

Fig. 7

```
  1 MQTLSIQHGT  LVTMDQYRRV  LGDSWVHVQD  GRIVALGVHA  ESVPPPADRV
 51 IDARGKVVLP  GFINAHTHVN  QILLRGGPSH  GRQFYDWLFN  VVYPGQKAMR
101 PEDVAVAVRL  YCAEAVRSGI  TTINENADSA  IYPGNIEAAM  AVYGEVGVRV
151 VYARMFFDRM  DGRIQGYVDA  LKARSPQVEL  CSIMEETAVA  KDRITALSDQ
201 YHGTAGGRIS  VWPAPATTTA  VTVEGMRWAQ  AFARDRAVMW  TLHMAESDHD
251 ERIHGMSPAE  YMECYGLLDE  RLQVAHCVYF  DRKDVRLLHR  HNVKVASQVV
301 SNAYLGSGVA  PVPEMVERGM  AVGIGTDNGN  SNDSANMIGD  MKFMAHIHRA
351 VHRDADVLTP  EKILEMATID  GARSLGMDHE  IGSIETGKRA  DLILLDLRHL
401 RRLSHHLAAT  IVFQAYGNEV  DTVLIDGNVV  MENRRLSFLP  PERELAFLEE
451 AQSRATAILQ  RANMVANPAW  RSL
```

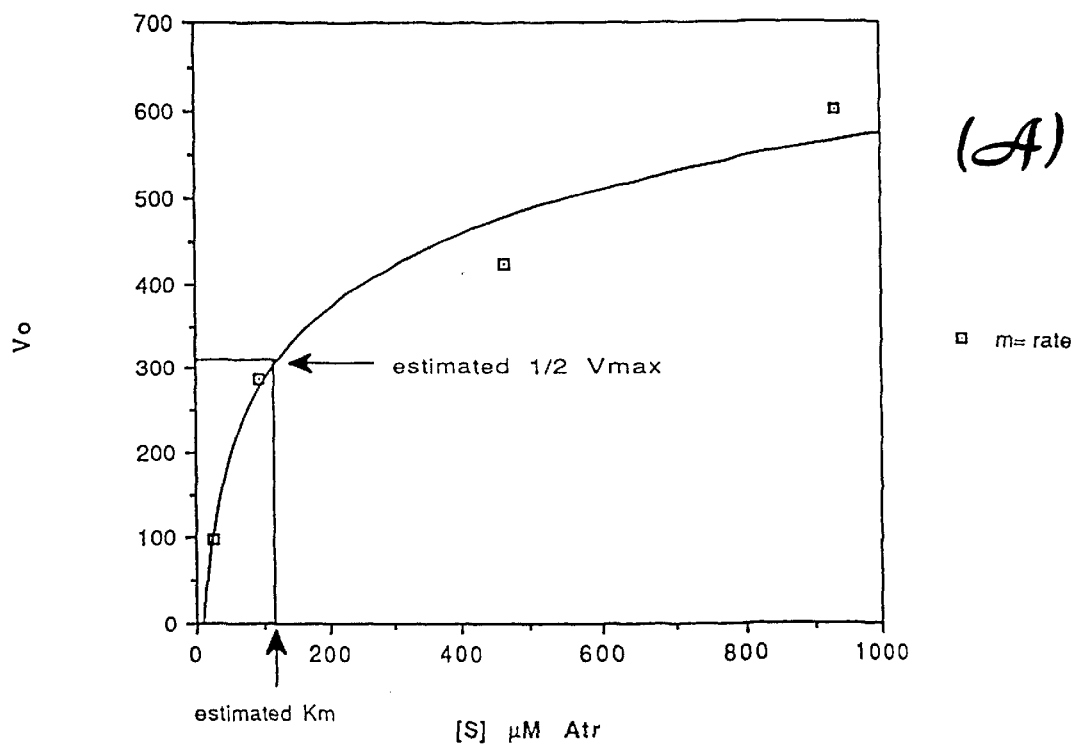
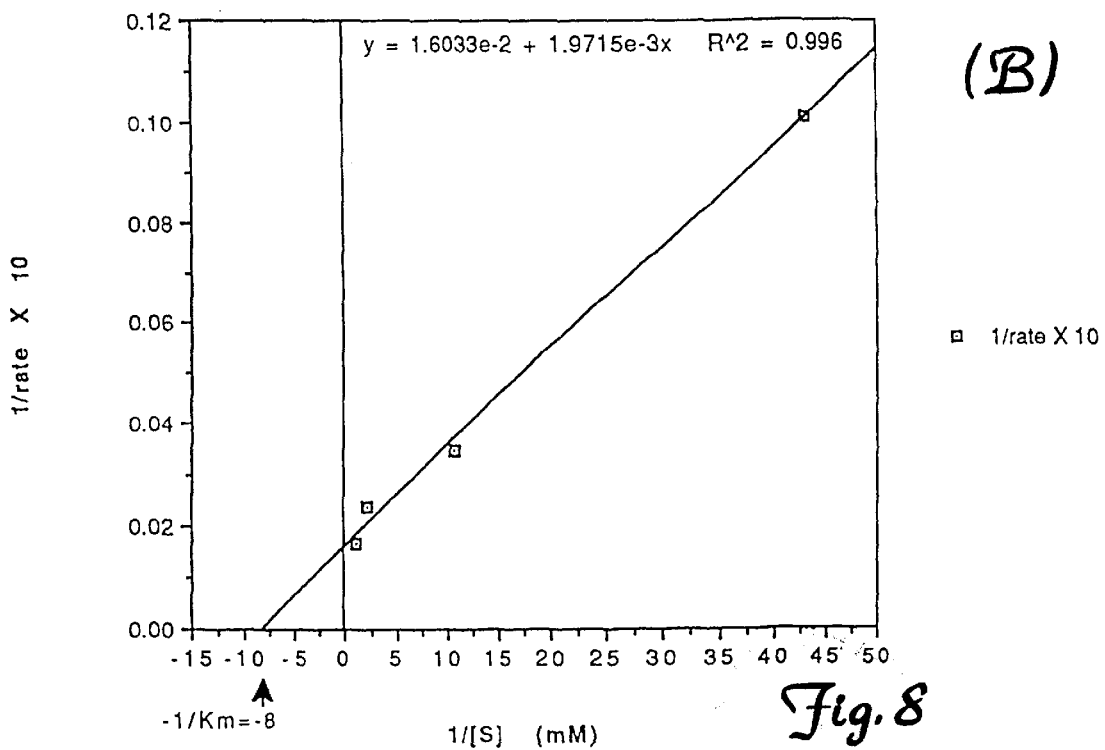
Fig. 8

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1858 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
CTCGGGTAAC TTCTTGAGCG CGGCCACAGC AGCCTTGATC ATGAAGGCGA GCATGGTGAC      60

CTTGACGCCG CTCTTTTCGT TCTCTTTGTT GAACTGCACG CGAAAGGCTT CCAGGTCGGT     120

GATGTCCGCG TCGTCGTGGT TGGTGACGTG CGGGATGACC ACCCAGTTGC GGTGCAGGTT     180

TTTCGATGGC ATAATATCTG CGTTGCGACG TGTAACACAC TATTGGAGAC ATATCATGCA     240

AACGCTCAGC ATCCAGCACG GTACCCTCGT CACGATGGAT CAGTACCGCA GAGTCCTTGG     300

GGATAGCTGG GTTCACGTGC AGGATGGACG GATCGTCGCG CTCGGAGTGC ACGCCGAGTC     360

GGTGCCTCCG CCAGCGGATC GGGTGATCGA TGCACGCGGC AAGGTCGTGT TACCCGGTTT     420

CATCAATGCC CACACCCATG TGAACCAGAT CCTCCTGCGC GGAGGGCCCT CGCACGGACG     480

TCAATTCTAT GACTGGCTGT TCAACGTTGT GTATCCGGGA CAAAAGGCGA TGAGACCGGA     540

GGACGTAGCG GTGGCGGTGA GGTTGTATTG TGCGGAAGCT GTGCGCAGCG GGATTACGAC     600

GATCAACGAA AACGCCGATT CGGCCATCTA CCCAGGCAAC ATCGAGGCCG CGATGGCGGT     660

CTATGGTGAG GTGGGTGTGA GGGTCGTCTA CGCCCGCATG TTCTTTGATC GGATGGACGG     720

GCGCATTCAA GGGTATGTGG ACGCCTTGAA GGCTCGCTCT CCCCAAGTCG AACTGTGCTC     780

GATCATGGAG GAAACGGCTG TGGCCAAAGA TCGGATCACA GCCCTGTCAG ATCAGTATCA     840

TGGCACGGCA GGAGGTCGTA TATCAGTTTG GCCCGCTCCT GCCACTACCA CGGCGGTGAC     900

AGTTGAAGGA ATGCGATGGG CACAAGCCTT CGCCCGTGAT CGGGCGGTAA TGTGGACGCT     960

TCACATGGCG GAGAGCGATC ATGATGAGCG GATTCATGGG ATGAGTCCCG CCGAGTACAT    1020

GGAGTGTTAC GGACTCTTGG ATGAGCGTCT GCAGGTCGCG CATTGCGTGT ACTTTGACCG    1080

GAAGGATGTT CGGCTGCTGC ACCGCCACAA TGTGAAGGTC GCGTCGCAGG TTGTGAGCAA    1140
```

-continued

```
TGCCTACCTC GGCTCAGGGG TGGCCCCCGT GCCAGAGATG GTGGAGCGCG GCATGGCCGT    1200

GGGCATTGGA ACAGATAACG GGAATAGTAA TGACTCCGCA ACATGATCG GAGACATGAA     1260

GTTTATGGCC CATATTCACC GCGCGGTGCA TCGGGATGCG GACGTGCTGA CCCCAGAGAA    1320

GATTCTTGAA ATGGCGACGA TCGATGGGGC GCGTTCGTTG GGAATGGACC ACGAGATTGG    1380

TTCCATCGAA ACCGGCAAGC GCGCGGACCT TATCCTGCTT GACCTGCGTC ACCTCAGACG    1440

ACTCTCACAT CATTTGGCGG CCACGATCGT GTTTCAGGCT TACGGCAATG AGGTGGACAC    1500

TGTCCTGATT GACGGAAACG TTGTGATGGA GAACCGCCGC TTGAGCTTTC TTCCCCCTGA    1560

ACGTGAGTTG GCGTTCCTTG AGGAAGCGCA GAGCCGCGCC ACAGCTATTT TGCAGCGGGC    1620

GAACATGGTG GCTAACCCAG CTTGGCGCAG CCTCTAGGAA ATGACGCCGT TGCTGCATCC    1680

GCCGCCCCTT GAGGAAATCG CTGCCATCTT GGCGCGGCTC GGATTGGGGG GCGGACATGA    1740

CCTTGATGGA TACAGAATTG CCATGAATGC GGCACTTCCG TCCTTCGCTC GTGTGGAATC    1800

GTTGGTAGGT GAGGGTCGAC TGCGGGCGCC AGCTTCCCGA AGAGGTGAAA GGCCCGAG     1858
```

(2) INFORMATION FOR SEQ ID NO:2:

(i) SEQUENCE CHARACTERISTICS:
        (A) LENGTH: 473 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Ala Asp
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Val Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Asp
        115                 120                 125

Ser Ala Ile Tyr Pro Gly Asn Ile Glu Ala Ala Met Ala Val Tyr Gly
    130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
    210                 215                 220
```

```
Gly Met Arg Trp Ala Gln Ala Phe Ala Arg Asp Arg Ala Val Met Trp
225                 230                 235                 240

Thr Leu His Met Ala Glu Ser Asp His Asp Glu Arg Ile His Gly Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Ala Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Leu
385                 390                 395                 400

Arg Arg Leu Ser His His Leu Ala Ala Thr Ile Val Phe Gln Ala Tyr
                405                 410                 415

Gly Asn Glu Val Asp Thr Val Leu Ile Asp Gly Asn Val Val Met Glu
                420                 425                 430

Asn Arg Arg Leu Ser Phe Leu Pro Pro Glu Arg Glu Leu Ala Phe Leu
        435                 440                 445

Glu Glu Ala Gln Ser Arg Ala Thr Ala Ile Leu Gln Arg Ala Asn Met
    450                 455                 460

Val Ala Asn Pro Ala Trp Arg Ser Leu
465                 470
```

US 6,284,522 B1

ISOLATED AND PURIFIED DNA MOLECULE AND PROTEIN FOR THE DEGRADATION OF TRIAZINE COMPOUNDS

STATEMENT OF GOVERNMENT RIGHTS

This invention was made with government support from the United States Department of Agriculture-BARD program, Grant No.94-34339-112. The government may have certain rights in this invention.

BACKGROUND OF THE INVENTION

Atrazine [2-chloro-4-(ethylamino)-6-(isopropylamino)-1,3,5-triazine)] is a widely used s-triazine (i.e., symmetric triazine) herbicide for the control of broad-leaf weeds. Approximately 800 million pounds were used in the United States between 1980 and 1990. As a result of this widespread use, for both selective and nonselective weed control, atrazine and other s-triazine derivatives have been detected in ground and surface water in several countries.

Numerous studies on the environmental fate of atrazine have shown that atrazine is a recalcitrant compound that is transformed to $CO_2$ very slowly, if at all, under aerobic or anaerobic conditions. It has a water solubility of 33 mg/l at 27° C. Its half-life (i.e., time required for half of the original concentration to dissipate) can vary from about 4 weeks to 57 weeks if in soils at low concentration (i.e., less than about 2 parts per million (ppm)). High concentrations of atrazine, such as those occurring in spill sites, have been reported to dissipate even more slowly.

As a result of its widespread use, atrazine is often detected in ground water and soils in concentrations exceeding the maximum contaminant level (MCL) of 3 $\mu$g/l (i.e., 3 parts per billion (ppb)), a regulatory level that took effect in 1992. Point source spills of atrazine have resulted in levels as high as 25 ppb in some wells. Levels of up to 40,000 mg/l (i.e., 40,000 parts per million (ppm)) atrazine have been found in the soil of spill sites more than ten years after the spill incident. Such point source spills and subsequent runoff can cause crop damage and ground water contamination.

There have been numerous reports of the isolation of s-triazine-degrading microorganisms (see, e.g., Behki et al., *J. Agric. Food Chem.*, 34, 746–749 (1986); Behki et al., *Appl. Environ. Microbiol.*, 59, 1955–1959 (1993); Cook, *FEMS Microbiol. Rev.*, 46, 93–116 (1987); Cook et al., *J. Agric. Food Chem.*, 29, 1135–1143 (1981); Erickson et al., *Critical Rev. Environ. Cont.*, 19, 1–13 (1989); Giardina et al., *Agric. Biol. Chem.*, 44, 2067–2072 (1980); Jessee et al., *Appl. Environ. Microbiol.*, 45, 97–102 (1983); Mandelbaum et al., *Appl. Environ. Microbiol.*, 61, 1451–1457 (1995); Mandelbaum et al., *Appl. Environ. Microbiol.*, 59, 1695–1701 (1993); Mandelbaum et al., *Environ. Sci. Technol.*, 27, 1943–1946 (1993); Radosevich et al., *Appl. Environ. Microbiol.*, 61, 297–302 (1995); and Yanze-Kontchou et al., *Appl. Environ. Microbiol.*, 60, 4297–4302 (1994)). Many of the organisms described, however, failed to mineralize atrazine (see, e.g., Cook, *FEMS Microbiol. Rev.*, 46, 93–116 (1987); and Cook et al., *J. Agric. Food Chem.*, 29, 1135–1143 (1981)). While earlier studies have reported atrazine degradation only by mixed microbial consortia, more recent reports have indicated that several isolated bacterial strains can degrade atrazine. For example, we previously reported the isolation of a pure bacterial culture, identified as Pseudomonas sp. strain ADP (Mandelbaum et al., *Appl. Environ. Microbiol.*, 61, 1451–1457 (1995); Mandelbaum et al., *Appl. Environ. Microbiol.*, 59, 1695–1701 (1993); and Mandelbaum et al., *Environ. Sci. Technol.*, 27, 1943–1946 (1993)), which degraded a high concentration of atrazine (>1,000 $\mu$g/ml) under growth and non-growth conditions. See also, Radosevich et al., *Appl. Environ. Microbiol.*, 61, 297–302 (1995) and Yanze-Kontchou et al., *Appl. Environ. Microbiol.*, 60, 4297–4302 (1994). Pseudomonas sp. strain ADP (Atrazine Degrading Pseudomonas) uses atrazine as a sole source of nitrogen for growth. The organism completely mineralizes the s-triazine ring of atrazine under aerobic growth conditions. That is, this bacteria is capable of degrading the s-triazine ring and mineralizing organic intermediates to inorganic compounds and ions (e.g., $CO_2$).

Little information is available concerning the genes and enzymes involved in the metabolism of s-triazine compounds. Although genes that encode the enzymes for melamine (2,4,6-triamino-s-triazine) metabolism have been isolated from a Pseudomonas sp. strain, and that encode atrazine degradation activity from Rhodococcus sp. strains, to date there have been no reports identifying the genes encoding atrazine dechlorination.

SUMMARY OF THE INVENTION

The present invention provides an isolated and purified DNA molecule that encodes atrazine chlorohydrolase. The DNA molecule hybridizes to DNA complementary to DNA having the sequence shown in FIG. 6 (SEQ ID NO:1), beginning at position 236 and ending at position 1655, under the stringency conditions of hybridization in buffer containing 0.25 M $Na_2HPO_4$, 7% SDS, 1% BSA, 1.0 mM EDTA at 65° C., followed by washing with 0.1% SDS and 0.1×SSC at 65° C. Preferably, the present invention provides an isolated and purified DNA molecule encoding the atrazine chlorohydrolase having an amino acid sequence shown in FIG. 7 (SEQ ID NO:2). Preferably, the DNA molecule has the nucleotide sequence shown in FIG. 6 (SEQ ID NO:1) beginning at position 236 and ending at position 1655. The present invention also provides a vector comprising the DNA molecule described herein, a transformed cell line, and isolated and purified oligonucleotides of about 7–300 nucleotides.

The present invention also provides an isolated and purified protein having a molecular weight of about 245 kilodaltons that converts atrazine to hydroxyatrazine. Preferably, this protein has the amino acid sequence shown in FIG. 7 (SEQ. ID NO:2). Also provided is an isolated and purified preparation of polyclonal antibodies produced from this isolated and purified protein.

The present invention also provides a method for the purification of atrazine chlorohydrolase in at least about 90% yield consisting of a step of adding ammonium sulfate to an aqueous cell-free extract of an atrazine chlorohydrolase-containing bacterium. This ammonium sulfate is present in an amount of no more than about 20% of saturation. Finally, the present invention provides a method for degrading s-triazine compounds.

BRIEF DESCRIPTION OF THE DRAWINGS

FIG. 2. Southern hybridization analysis of genomic DNA from Pseudomonas sp. strain ADP and other atrazine degrading microorganisms. A $^{32}$P-labelled 0.6 kb ApaI/PstI fragment from pMD4 was used as probe. Lanes: 1, EcoRI-digested genomic DNA from a consortium degrading atrazine (Stucki et al., *Water Res.*, 1, 291–296 (1995)); 2, EcoRI-digested genomic DNA from a newly isolated atrazine-degrading bacterium; 3, AvaI-digested genomic DNA from Pseiudomonas sp. strain ADP; 4, EcoRI-digested genomic DNA from Pseudomonas sp. strain ADP. Values in margin are in kilobase pairs.

FIG. 6. Nucleotide sequence of atzA (SEQ ID NO:1), beginning at position 236 and ending at position 1655. The complete nucleotide sequence of the approximately 1.9-kb AvaI DNA fragment, cloned in pMD4, was determined on both strands using subcloning and the primer walking method and PCR. The ORF designated atzA is indicated by the arrow and a potential Pseudomonas ribosome binding site is underlined. The double underlined sequence is the stop codon.

FIG. 7. Amino acid sequence of the AtzA enzyme (SEQ ID NO:2) determined by translating the atzA ORF.

FIG. 8. Enzyme kinetics. Michaelis Menton (A) and Lineweaver Burke (B) plots for purified AtzA. The estimated Km is 125 $\mu$M.

DETAILED DESCRIPTION OF THE INVENTION

Figure 1:
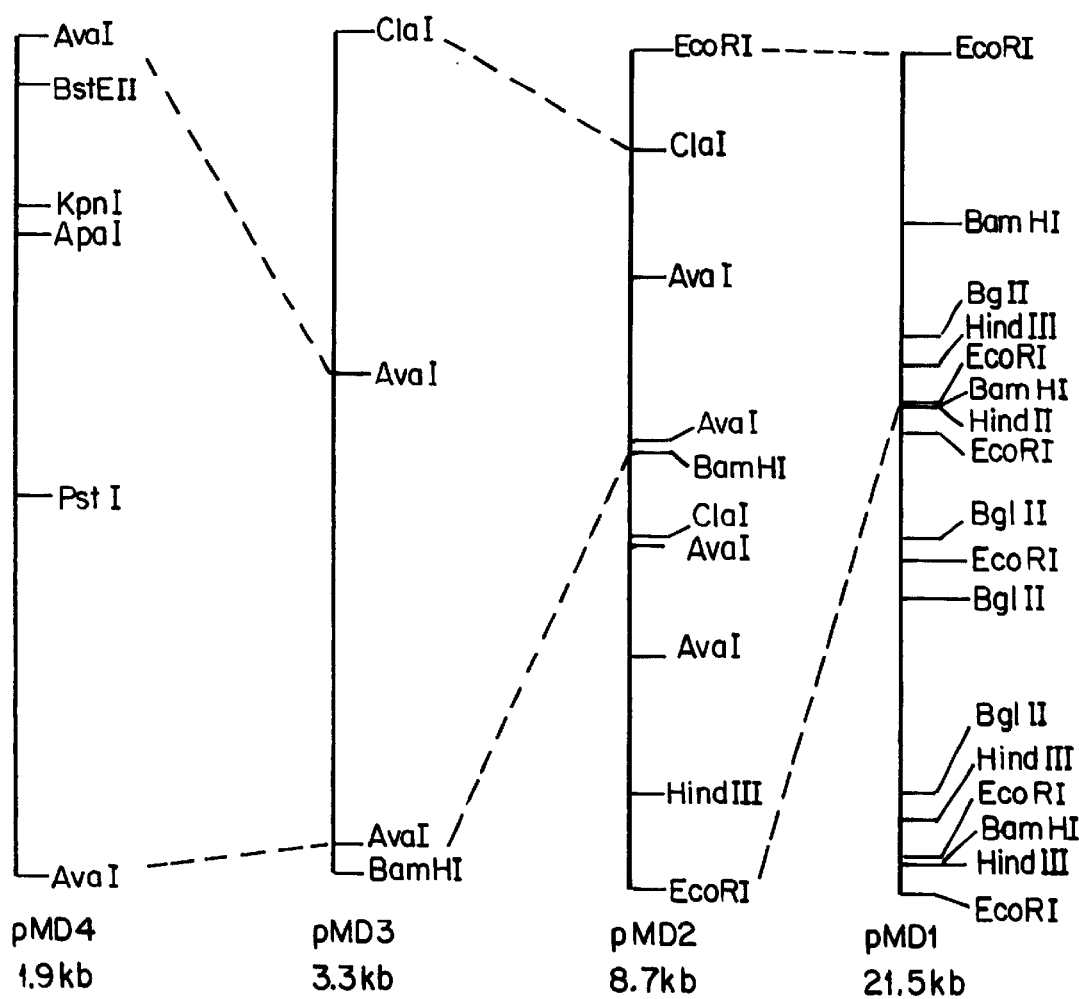
FIG. 1. Physical relationship of clones expressing atrazine degradation ability. Cosmid pMD1 is a 21.5 kb EcoRI fragment in pLAFR3. Plasmid pMD2 is a 8.7 kb EcoRI fragment from pMD1 cloned into pACYC184. Plasmid pMD3 is a 3.3 kb ClaI/Bam HI fragment from pMD2 cloned into pACYC184. Plasmid pMD4 is a 1.9 kb AvaI fragment from pMD3 cloned into pACYC184. All four clones express atrazine degrading activity in *Escherichia coli* DH5α.

The present invention provides an isolated and purified DNA molecule, and an isolated and purified protein, involved in the degradation of s-triazine compounds. More specifically, the isolated and purified DNA molecule and the protein it encodes are involved in the dechlorination of s-triazine compounds containing a chlorine atom and at least one alkylamino side chain. Such compounds have the following general formula:

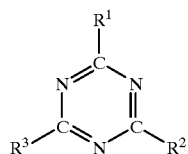

wherein $R^1$=Cl, $R^2$=$NR^4R^5$ (wherein $R^4$ and $R^5$ are each independently H or a $C_{1-3}$ alkyl group), and $R^3$=$NR^6R^7$ (wherein $R^6$ and $R^7$ are each independently H or a $C_{1-3}$ alkyl group), with the proviso that at least one of $R^2$ or $R^3$ is an alkylamino group. As used herein, an "alkylamino" group refers to an amine side chain with one or two alkyl groups attached to the nitrogen atom. Examples of such compounds include atrazine (2-chloro-4-ethylamino-6-isopropylamino-1,3,5-s-triazine), desethylatrazine (2-chloro-4-amino-6-isopropylamino-s-triazine), desisopropylatrazine (2-chloro-4-ethylamino-6-amino-s-triazine), and simazine (2-chloro-4,6-diethylamino-s-triazine).

Triazine degradation activity is localized to a 21.5-kb EcoRI fragment, and more specifically to a 1.9-kb AvaI fragment of the genome of Pseudomonas sp. ADP bacterium. Specifically, these genomic fragments are involved in s-triazine dechlorination. In fact, the rate of degradation of atrazine that results from the expression of these fragments in *E. coli* is comparable to that seen for native Pseudomonas sp. strain ADP; however, in contrast to what is seen with native Pseudomonas sp. strain ADP, this degradation is unaffected by the presence of inorganic nitrogen sources like ammonium chloride. This is particularly advantageous for regions contaminated with nitrogen-containing fertilizers, for example. The expression of atrazine degradation activity in the presence of inorganic nitrogen compounds broadens the potential use of recombinant organisms for biodegradation of atrazine in soil and water. Thus, the background in which these fragments are expressed can provide advantageous results.

The 1.9-kb AvaI genomic fragment includes the gene that encodes an enzyme that transforms atrazine to hydroxyatrazine, atrazine chlorohydrolase. As used herein, this gene is referred to as "atzA", whereas the protein that it encodes is referred to as "AtzA". Hydroxyatrazine formation in the environment was previously thought to result solely from the chemical hydrolysis of atrazine (Armstrong et al., *Environ. Sci. Technol.*, 2, 683–689 (1968); deBruijn et al., *Gene*, 27, 131–149 (1984); and Nair et al., *Environ. Sci. Technol.*, 26, 2298–2300 (1992)). In contrast to reports that the first step in atrazine degradation by environmental bacteria is dealkylation, this suggests that biological transformation of atrazine to hydroxyatrazine may be widespread in natural systems.

The AtzA protein can be purified to homogeneity (i.e., about 95% purity) in two steps involving precipitation in an aqueous $NH_4SO_4$ solution and anion exchange chromatography. Preferably, the aqueous $NH_4SO_4$ solution contains no more than about 20% $NH_4SO_4$, based on its saturation level in water, typically at about 4° C. Advantageously, the initial $NH_4SO_4$ precipitation step alone provides the protein in a level of purity of at least about 90%. It may be further purified using anion exchange chromatography, typically performed with DEAE-cellulose or DEAE Sepharose CL-6B, to separate, at least partially, different activities. Other chromatographic techniques that may be used in the purification of such enzymes include hydroxylapatite and gel filtration, preferably in combination with one or more of a variety of affinity chromatographic columns with varying degrees of specificity. Affinity columns that may be used include Affi-Gel Blue, ATP-agarose chromatography, heparin-Sepharose, ADP-agarose, PAP-agarose, Estradiol-17β-Sepharose, and p-hydroxyphenylacetic acid-agarose.

The availability of purified AtzA enzyme makes it possible to characterize the enzyme and to develop antibodies that can be used, for example, to screen DNA expression libraries. The fact that AtzA is precipitated from cell-free supernatants in such a low concentration of $NH_4SO_4$ is surprising and fortuitous and will facilitate the large scale production of AtzA for remediation technologies. For example, a 250 liter culture of recombinant *E. coli* could yield 10 kilograms wet cell paste that would give 50 liters of crude protein extract, which could be processed by adding ammonium sulfate to 20% saturation, followed by filtration to give 50 grams of purified protein. Even higher yields are possible with more optimized expression cassette components.

In addition, the ability of the AtzA enzyme to dechlorinate substrates such as atrazine and simazine, for example, make this protein unique and potentially very useful for environmental remediation of xenobiotic triazine compounds, particularly because it is very efficient. For example, a protein concentration of 50 mg/liter could degrade about 100 µM of atrazine to about 1 µM in about 1.35 hours, and about 30 ppm of atrazine to about 3 ppb in about 2.6 hours. Various environmental remediation techniques are known that utilize high levels of proteins. For example, proteins can be bound to immobilization supports, such as beads, particles, films, etc., made from latex polymers, alginate, polyurethane, plastic, glass, polystyrene, and other natural and man-made support materials. Such immobilized protein can be used in packed-bed columns for treating water effluents. Other environmental samples could also be treated with the protein of the present invention (e.g., soil samples).

Specifically, the present invention is directed to the isolation and expression of atrazine chlorohydrolase DNA as well as the characterization and production of an atrazine chlorohydrolase protein. To that end, the invention provides an isolated and purified DNA molecule encoding an atrazine chlorohydrolase protein (i.e., an enzyme) or biologically active derivative thereof. More preferably, the DNA molecule encodes the protein represented by the amino acid sequence shown in FIG. 7 (SEQ ID NO:2). Most preferably, the DNA molecule is represented by the complete nucleotide sequence shown in FIG. 6 (SEQ ID NO:1), beginning at position 236 and ending at position 1655. Isolated and purified proteins encoded by this DNA molecule that convert atrazine to hydroxyatrazine are also within the scope of the invention.

As used herein, the terms "isolated and purified" refer to in vitro isolation of a DNA molecule or protein from its natural cellular environment, and from association with other coding regions of the bacterial genome, so that it can be sequenced, replicated, and/or expressed. Preferably, the isolated and purified DNA molecules of the invention comprise a single coding region. Thus, the present DNA molecules are preferably those consisting of a DNA segment encoding an atrazine chlorohydrolase protein or biologically active derivative thereof. Although the DNA molecule includes a single coding region, it can contain additional nucleotides that do not detrimentally affect the function of the DNA molecule, i.e., the expression of the atrazine chlorohydrolase protein or biologically active derivative thereof. For example, the 5' and 3' untranslated regions may contain variable numbers of nucleotides. Preferably, additional nucleotides are outside the single coding region.

The present invention provides an isolated and purified DNA molecule that encodes atrazine chlorohydrolase protein and that hybridizes to a DNA molecule complementary to the DNA molecule shown in FIG. 7 (SEQ ID NO:1), beginning at position 236 and ending at position 1655, under high stringency hybridization conditions. As used herein, "high stringency hybridization conditions" refers to hybridization in buffer containing 0.25 M $Na_2HPO_4$ (pH 7.4), 7% sodium dedecyl sulfate (SDS), 1% bovine serum albumin (BSA), 1.0 mM ethylene diamine tetraacetic acid (EDTA, pH 8) at 65° C., followed by washing 3× with 0.1% SDS and 0.1×SSC (0.1×SSC contains 0.015 M sodium chloride and 0.0015 M trisodium citrate, pH 7.0) at 65° C.

The present invention also provides an isolated and purified (preferably chemically synthesized) oligonucleotide of at least about seven nucleotides (i.e., a primer or a probe preferably containing no more than about 300 nucleotides) which hybridizes to the DNA molecules of the present invention, preferably the DNA molecule shown in FIG. 7, beginning at position 236 and ending at position 1655, under the high stringency hybridization conditions described above. Oligonucleotide probes and primers are segments of labeled, single-stranded DNA which will hybridize, or noncovalently bind, with complementary single-stranded DNA to be identified. If desired, the probe and primer can be labeled with any suitable label known to those skilled in the art, including radioactive and nonradioactive labels. Typical radioactive labels include $^{32}P$, $^{125}I$, $^{35}S$, and the like. Non-radioactive labels include, for example, ligands such as biotin or digoxigenin as well as enzymes such as phosphatase or peroxidases, or the various chemiluminescers such as luciferin, or fluorescent compounds like fluorescein and its derivatives. The probe or primer may also be labeled at both ends with different types of labels for ease of separation, as, for example, by using an isotopic label at one end and a biotin label at the other end.

As used herein, the terms atrazine chlorohydrolase (AtzA) protein, atrazine chlorohydrolase (AtzA) enzyme, or simply atrazine chlorohydrolase (AtzA), are used interchangeably, and refer to an atrazine chlorohydrolase enzyme involved in the degradation of atrazine and similar molecules as discussed above. A "biologically active derivative thereof" is an atrazine chlorohydrolase that is modified by amino acid deletion, addition, substitution, or truncation, or that has been chemically derivatized, but that nonetheless converts atrazine to hydroxyatrazine. For example, it is known in the art that substitutions of aliphatic amino acids such as alanine, valine, and isoleucine with other aliphatic amino acids can often be made without altering the structure or function of a protein. Similarly, substitution of aspartic acid for glutamic acid, in regions other than the active site of an enzyme, are likely to have no appreciable affect on protein structure or function. The term "biologically active derivative" is intended to include AtzA's as thus modified. The term also includes fragments, variants, analogs or chemical derivatives of AtzA enzyme. The term "fragment" is meant to refer to any polypeptide subset of AtzA enzyme. Fragments can be prepared by subjecting AtzA to the action of any one of a number of commonly available proteases, such as trypsin, chymotrypsin or pepsin, or to chemical cleavage agents, such as cyanogen bromide. The term "variant" is meant to refer to a molecule substantially similar in structure and function to either the entire AtzA molecule or to a fragment thereof. A molecule is said to be "substantially similar" to AtzA or a fragment thereof if both molecules have substantially similar amino acid sequences, preferably greater than about 80% sequence identity, or if the three-dimensional backbone structures of the molecules are superimposable, regardless of the level of identity between the amino acid sequences. Thus, provided that two molecules possess atrazine chlorohydrolase activity, they are considered variants as that term is used herein even if the structure of one of the molecules is not found in the other, or if the sequences of amino acid residues are not identical. The term "analog" is meant to refer to a protein that differs structurally from the wild type enzyme AtzA, but converts atrazine to hydroxyatrazine.

The present invention also provides a vector comprising an isolated and purified DNA molecule encoding atrazine chlorohydrolase, preferably the atrazine chlorohydrolase having the amino acid sequence shown in FIG. 7 (SEQ ID NO:2) beginning at position 236 and ending at position 1655. That is, preferably, the vector includes a single atrazine chlorohydrolase coding region. It can also include other DNA segments operably linked to the coding sequence in an expression cassette as required for expression of atrazine chloprohydrolase, such as a promoter region operably linked to the 5' end of the coding DNA sequence, a selectable marker gene, a reporter gene, and the like.

The present invention also provides a recombinant cell line, preferably a bacterial cell line, the genome of which has been augmented by chromosomally integrated non-native DNA encoding atrazine chlorohydrolase as herein described. For example, DNA that expresses atrazine chlorohydrolase and is isolated from a Pseudomonas sp. bacterial strain, can be transferred to a non-Pseudomonas sp. strain, such as other Pseudomonas bacterial strains as well as bacterial genera Escherichia, Rhizobium, Bacillus, Bradyrhizobium, Arthrobacter, Alcaligenes, and other rhizosphere and non-rhizosphere soil microbe strains. Such strains may possess advantageous properties not present in the native Pseudomonas sp. strain. For example, inorganic nitrogen-containing fertilizers in soils can shut off activity in the native Pseudomonas sp. strain, but not in other strains such as $E.$ $coli.$ The present invention also provides a preparation of polyclonal antibodies produced in response to the AtzA protein of the present invention. Preferably, the polyclonal antibodies are of the IgG class, although other classes are possible. The polyclonal antibody preparation can be used, for example, to screen bacteria for the presence of the AtzA protein. It can also be used in the isolation of the atzA gene and detection of the AtzA protein expressed in another host organism. Furthermore, the antibody can also be bound to immobilization supports, such as commercially available matrices like Activated Affinity Supports Affi-Gel 15+10 by Biorad Laboratories (Hercules, Calif.) and used in affinity chromatography columns for purifying the AtzA protein.

Several different methods are available for isolating atzA DNA. This includes, for example, purifying enzyme protein, and then subjecting it to amino acid microsequencing, either directly or after limited cleavage. The partial amino acid sequence that is obtained can be used to design degenerate oligonucleotide probes or primers for use in the generation of unique, nondegenerate nucleotide sequences by polymerase chain reaction (PCR), sequences that can in turn be used as probes for screening DNA libraries. Antibodies raised against purified protein may also be used to isolate DNA clones from DNA expression libraries. Alternatively, the sequences of DNA molecules for related enzymes may be used as starting points in a cloning strategy. This method is often referred to as "cloning by homology." Another way of utilizing sequence information from different species is to take advantage of shorter areas of high sequence homology among related DNA molecules from different species and to perform the polymerase chain reaction sequencing amplification method (PCR) to obtain "species-specific" nondegenerate nucleotide sequences. Such a sequence can then be used for DNA library screening or even for direct PCR-based DNA cloning.

Using standard biochemical procedures well-known in the art, oligonucleotide probes can be used to detect and amplify an atzA DNA molecule in a wide variety of samples. For example, Southern or Northern blotting hybridization techniques using labeled probes can be used. Alternatively, PCR techniques can be used, and nucleic acid sequencing of amplified PCR products can be used to detect mutations in the DNA.

Detection of the DNA can involve the use of PCR using novel primers. The method involves treating extracted DNA to form single-stranded complementary strands, treating the separate complementary strands of DNA with two oligonucleotide primers, extending the primers to form complementary extension products that act as templates for synthesizing the desired nucleic acid molecule, and detecting the amplified molecule.

DNA primer pairs of known sequence positioned 10–300 base pairs apart that are complementary to the plus and minus strands of the DNA to be amplified can be prepared by well known techniques for the synthesis of oligonucleotides. Conveniently, one end of each primer can be extended and modified to create restriction endonuclease sites when the primer is annealed to the target DNA. These restriction sites facilitate the use of the amplified product for cloning at a later date. The PCR reaction mixture can contain the target DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the target DNA at an elevated temperature, cooling of the reaction mixture, and polymerization with the DNA polymerase.

Cloning of the open reading frame encoding atzA into the appropriate replicable vectors allows expression of the gene product, AtzA enzyme, and makes the coding region available for further genetic engineering. Expression of AtzA enzyme or portions thereof, is useful because these gene products can be used to degrade atrazine and similar compounds, as discussed above.

1. Isolation of DNA

DNA containing the region encoding AtzA may be obtained from a DNA library, containing either genomic or complementary DNA, prepared from bacteria believed to possess the atzA DNA and to express it at a detectable level. Libraries are screened with appropriate probes designed to identify the DNA, either genomic or complementary DNA, of interest. Preferably, for DNA libraries, suitable probes include oligonucleotides that consist of known or suspected portions of the atzA DNA from the same or different species; and/or complementary or homologous DNA molecules or fragments thereof that consist of the same or a similar DNA. For DNA expression libraries (which express the protein), suitable probes include monoclonal or polyclonal antibodies that recognize and specifically bind to the AtzA protein. Appropriate probes for screening DNA libraries include, but are not limited to, oligonucleotides, cDNA molecules, or fragments thereof that consist of the same or a similar gene, and/or homologous genomic DNA molecules or fragments thereof. Screening the DNA library with the selected probe may be accomplished using standard procedures.

Screening DNA libraries using synthetic oligonucleotides as probes is a preferred method of practicing this invention. The oligonucleotide sequences selected as probes should be of sufficient length and sufficiently unambiguous to minimize false positives. The actual nucleotide sequence(s) of the probe(s) is usually designed based on regions of the atzA DNA that have the least codon redundancy. The oligonucleotides may be degenerate at one or more positions, i.e., two or more different nucleotides may be incorporated into an oligonucleotide at a given position, resulting in multiple synthetic oligonucleotides. The use of degenerate oligonucleotides is of particular importance where a library is screened from a species in which preferential codon usage is not known.

The oligonucleotide can be labeled such that it can be detected upon hybridization to DNA in the library being screened. A preferred method of labeling is to use ATP and polynucleotide kinase to radiolabel the 5' end of the oligonucleotide. However, other methods may be used to label the oligonucleotide, including, but not limited to, biotinylation or enzyme labeling.

Of particular interest is the atzA nucleic acid that encodes a full-length mRNA transcript, including the complete coding region for the gene product, AtzA enzyme. Nucleic acid containing the complete coding region can be obtained by screening selected DNA libraries using the deduced amino acid sequence. An alternative means to isolate the DNA encoding AtzA enzyme is to use PCR methodology. This method requires the use of oligonucleotide primer probes that will hybridize to the DNA encoding AtzA.

2. Insertion of DNA into a Vector

The nucleic acid containing the atzA coding region is preferably inserted into a replicable vector for further cloning (amplification of the DNA) or for expression of the gene product, AtzA enzyme. Many vectors are available, and selection of the appropriate vector will depend on: 1) whether it is to be used for DNA amplification or for DNA expression; 2) the size of the nucleic acid to be inserted into the vector; and 3) the host cell to be transformed with the vector. Most expression vectors are "shuttle" vectors, i.e., they are capable of replication in at least one class of organism but can be transfected into another organism for expression. Each replicable vector contains various structural components depending on its function (amplification of DNA or expression of DNA) and the host cell with which it is compatible. These components are described in detail below.

Construction of suitable vectors employs standard ligation techniques known in the art. Isolated plasmids or DNA fragments are cleaved, tailored, and relegated in the form desired to generate the plasmids required. Typically, the ligation mixtures are used to transform *E. coli* DH5α and successful transformants are selected by ampicillin or tetracycline resistance where appropriate. Plasmids from the transformants are prepared, analyzed by restriction endonuclease digestion, and/or sequenced by methods known in the art. See, e.g., Messing et al., *Nucl. Acids Res.*, 9, 309 (1981) and Maxam et al., *Methods in Enzymology*, 65, 499 (1980).

Replicatable cloning and expression vector components generally include, but are not limited to, one or more of the following: a signal sequence, an origin of replication, one or more marker genes, and a promoter. Such vector components are well known to one of skill in the art. For example, a signal sequence may be used to facilitate extracellular transport of a cloned protein. To this end, the atzA gene product, AtzA enzyme, may be expressed not only directly, but also as a fusion product with a heterologous polypeptide, preferably a signal sequence or other polypeptide having a specific cleavage site at the N-terminus of the cloned protein. The signal sequence may be a component of the vector, or it may be a part of the atzA DNA that is inserted into the vector. The heterologous signal sequence selected should be one that is recognized and processed (i.e., cleaved by a signal peptidase) by the host cell. For prokaryotic host cells, a prokaryotic signal sequence may be selected, for example, from the group of the alkaline phosphatase, penicillinase, lpp or heat-stable intertoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, phages, and viral systems. The origin of replication from the plasmid pBR322 is suitable for most Gram-negative bacteria, for example.

Expression and cloning vectors may contain a marker gene, also termed a selection gene or selectable marker. This gene encodes a protein necessary for the survival or growth of transformed host cells grown in a selective culture medium. Host cells not transformed with the vector containing the selection gene will not survive in the culture medium. Typical selection genes encode proteins that: (a) confer resistance to antibiotics or other toxins, e.g., ampicillin, neomycin, methotrexate, streptomycin or tetracycline; (b) complement auxotrophic deficiencies; or (c) supply critical nutrients not available from complex media, e.g., the gene encoding D-alanine racemase for Bacillus. One example of a selection scheme utilizes a drug to arrest growth of a host cell. Those cells that are successfully transformed with a heterologous gene express a protein conferring drug resistance and thus survive the selection regimen.

Expression and cloning vectors usually contain a promoter that is recognized by the host organism and is operably linked to the atzA nucleic acid. Promoters are untranslated sequences located upstream (5') to the start codon of a structural gene (generally within about 100 to 1000 bp) that control the transcription and translation of a particular nucleic acid sequence, such as the atzA nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. In contrast, constitutive promoters produce a constant level of transcription of the cloned DNA segment.

At this time, a large number of promoters recognized by a variety of potential host cells are well known in the art. Promoters are removed from their source DNA using a restriction enzyme digestion and inserted into the cloning vector using standard molecular biology techniques. Native or heterologous promoters can be used to direct amplification and/or expression of atzA DNA. Heterologous promoters are preferred, as they generally permit greater transcription and higher yields of expressed protein as compared to the native promoter. Well-known promoters suitable for use with prokaryotic hosts include the beta-lactamase and lactose promoter systems, alkaline phosphatase, a tryptophan (trp) promoter system, and hybrid promoters such as the tac promoter. Such promoters can be ligated to atzA DNA using linkers or adapters to supply required restriction sites. Promoters for use in bacterial systems may contain a Shine-Dalgamo sequence for RNA polymerase binding.

The genetically engineered plasmid of the invention can be used to transform a host cell. Typically, prokaryotic host cells are used in the expression system according to the invention, although eukaryotic cells may also be used. Suitable prokaryotes include eubacteria, such as Gram-negative or Gram-positive organisms, for example, *E. coli*, Bacilli such as *B. subtilis*, Pseudomonas species such as *P. aeruginosa*, *Salmonella typhimurium*, or *Serratia marcsecans*. Preferably the host cell should secrete minimal amounts of proteolytic enzymes. Alternatively, in vitro methods of cloning, e.g., PCR or other nucleic acid polymerase reactions, are suitable.

In addition to prokaryotes, eukaryotic microbes such as filamentous fungi or yeast are suitable hosts for atzA-encoding vectors. *Saccaroniyces cerevisiae*, or common baker's yeast, is the most commonly used among lower eukaryotic host microorganisms. However, a number of other genera, species, and strains are commonly available and useful herein, such as *Schizosaccaromyces pombe*, Kluyveromyces hosts such as, e.g., *K. lactis, K. fragilis, K. bulgaricus, K. thermotolerans*, and *K. marxianus*, yarrowia, *Pichia pastoris*, Candida, *Trichoderma reesia, Neurospora crassa*, and filamentous fungi such as, e.g., Neurospora, Penicillium, Tolypocladium, and Aspergillus hosts such as *A. nidulans*.

4. Transfection and Transformation

Host cells are transfected and preferably transformed with the above-described expression or cloning vectors of this invention and cultured in conventional nutrient media modified as appropriate for inducing promoters, selecting transformants, or amplifying the genes encoding the desired sequences. Transfection refers to the taking up of an expression vector by a host cell whether or not any coding sequence are in fact expressed. Numerous methods of transfection are known to the ordinarily skilled artisan, for example, the calcium phosphate precipitation method and electroporation are commonly used. Successful transfection is generally recognized when any indication of the operation of the vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. Calcium chloride is generally used for prokaryotes or other cells that contain substantial cell-wall barriers. Transformations into yeast are typically carried out according to the method of Van Solingen et al., *J. Bact.*, 130, 946 (1977) and Hsiao et al., *Proc. Natl. Acad. Sci. (USA)*, 78 3829 (1979). However, other methods for introducing DNA into cells such as by nuclear injection, electroporation, or protoplast fusion may also be used.

5. Cell Culture

Prokaryotic cells used to produce the atzA gene product, atzA protein, are cultured in suitable media, as described generally in Maniatis et al., *Molecular Cloning: A Laboratory Manual*; Cold Spring Harbor Press: Cold Spring Harbor, N.Y. (1989). Any necessary supplements may also be included at appropriate concentrations that would be known to those skilled in the art. The culture conditions, such as temperature, pH, and the like, are those previously used with the host cell selected for expression, and will be apparent to those skilled in the art. Induction of cells, to cause expression of the AtzA protein, is accomplished using the procedures required by the particular expression system selected. The host cells referred to in this disclosure encompass in in vitro culture as well as cells that are within a host animal. Cells are harvested, and cell extracts are prepared, using standard laboratory protocols. The AtzA protein can be isolated from cell extracts. Optionally, cell extracts may be assayed directly for atrazine degradation activity.

AtzA variants in which residues have been deleted, inserted, or substituted are recovered in the same fashion as native AtzA enzyme, taking account of any substantial changes in properties occasioned by the variation. For example, preparation of an AtzA fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal anti-AtzA column can be employed to absorb the AtzA variant by binding it to at least one remaining immune epitope.

Alternatively, the AtzA enzyme may be purified by affinity chromatography using a purified AtzA-IgG coupled to a (preferably) immobilized resin such as Affi-Gel 10 (Bio-Rad, Richmond, Calif.) or the like, by means well-known in the art. A protease inhibitor such as phenyl methyl sulfonyl fluoride (PMSF) also may be useful to inhibit proteolytic degradation during purification, and antibiotics may be included to prevent the growth of adventitious contaminants.

General atrazine chlorohydrolase activity may be assayed by: monitoring the degradation of substrates like atrazine and simazine using HPLC; monitoring the clearing of atrazine on plates; monitoring the amount of chlorine released, as described by Bergman et al., *Anal. Chem.*, 29, 241–243 (1957); evaluating the derivitized product using gas chromatography and/or mass spectroscopy.

The invention will be further described by reference to the following detailed examples.

EXAMPLES

Materials and Methods

Bacterial strains and growth conditions. Pseudomonas sp. strain ADP (Mandelbaum et al., *Appl. Environ. Microbiol.*, 59, 1695–1701 (1993)) was grown at 37° C. on modified minimal salt buffer medium, containing 0.5% (wt/vol) sodium citrate dihydrate. The atrazine stock solution was prepared as described in Mandelbaum et al., *Appl. Environ. Microbiol.*, 61, 1451–1457 (1995)). *Escherichia coli* DH5α was grown in Luria-Bertani (LB) or M63 minimal medium, which are described in Maniatis et al., *Molecular Cloning: A Laboratory Manual*; Cold Spring Harbor Press: Cold Spring Harbor, N.Y. (1989). Tetracycline (15 µg/ml), kanamycin (20 µg/ml), and chloramphenicol 30 (µg/ml) were added as required.

Genomic library construction. Genomic DNA from Pseudomonas sp. strain ADP was isolated as follows. Briefly, cells grown as described above were centrifuged at 10,000×g for 10 minutes at 4° C., washed once in TEN buffer (50 mM Tris, 10 mM disodium EDTA, 50 mM NaCl, pH 8.0), and suspended in TEN buffer. Lysozyme (Sigma Chemical Co., St. Louis, Mo.) was added to a final concentration of 0.5 mg/ml, and cell suspensions were incubated at 37° C. for 30 minutes. Predigested protease solution (2 ml; 5 mg of protease [Type X; Sigma] per ml in TEN buffer heated at 37° C. for 1 hour) was added, and the suspensions were incubated at 37° C. for 30 minutes. A 2-ml fraction of 20% (wt/vol) Sarkosyl (N-lauroylsarcosine; Sigma) was added, and the mixtures were incubated at 37° C. for 1 hour. CsCl (31 g), 7.5 ml of TEN buffer, and 1.6 ml of ethidium bromide solution (10 mg/ml) were added to the cell lysates; and the mixtures were centrifuged at 40,000 rpm for 48 hours at 20° C. in a fixed-angle rotor (60 Ti; Beckman Instruments, Inc., Fullerton, Calif.). The high molecular weight DNA band was removed, and the DNA was repurified by ethidium bromide equilibrium density centrifugation, as described above. Genomic DNA was partially digested with EcoRI and size-selected by using sucrose density gradient centrifugation as described in Maniatis et al., *Molecular Cloning: A Laboratory Manual*; Cold Spring Harbor Press: Cold Spring Harbor, N.Y. (1989). DNA fragments, 18–22 kb in size, were ligated into EcoRi-digested cosmid vector pLAFR3, which is described in Staskawicz et al., *J. Bacteriol.*, 169, 5789–5794 (1987). Ligated DNA was packaged in vitro using the Packagene DNA packaging system (Promega, Madison, Wis.). *E. coli* DH5α was transfected with the packaging mix and colonies were selected on LB medium containing 15 µg/ml tetracycline and 50 µg/ml 5-bromo-4-chloro-3-indolyl-β-D-galactopyranoside (X-Gal). The final library contained 2000 clones.

Library screening. All colonies from the genomic DNA library were replica-plated onto LB medium containing 15 µg/ml tetracycline and 500 µg/ml crystalline atrazine. Plates were incubated at 37° C. for two weeks. Colonies expressing atrazine degradation activity had clearing zones surrounding them due to atrazine metabolism in the vicinity of the colony.

DNA manipulations. Subcloning, plasmid and cosmid DNA isolation procedures, Southern blotting, and hybridizations were performed as described in Maniatis et al., *Molecular Cloning: A Laboratory Manual*; Cold Spring Harbor Press: Cold Spring Harbor, N.Y. (1989). Transformation of *E. coli* DH5α was done according to the method of Hanahan, *DNA Cloning Vol. II*; D. M. Glover; Ed.; IRL Press Limited: Oxford, England; p. 120 (1985). Specifically, plasmid pACYC184, which is described in Chang et al., *J. Bacteriol.*, 134, 1141–1156 (1978) was used as the vector for all subcloning steps.

Tn5 mutagenesis. Random Tn5 mutagenesis, using λ::Tn5 (λ 467, b221 rex:Tn5 c1857, Oam29, Pam80) was done as described by de Bruijn et al., *Gene*, 27, 131–149 (1984). *E. coli* strain SE5000 was used as the host for cosmid pMD1 and plasmid MD2 during mutagenesis. Tn5 insertions in cloned, insert DNA were identified and mapped by restriction enzyme analysis and by Southern hybridization.

DNA Sequencing. The nucleotide sequence of the approximately 1.9-kb AvaI DNA fragment in vector pACYC184, designated pMD4, was determined on both strands. DNA was sequenced by using a PRISM Ready Reaction DyeDeoxy Terminator Cycle Sequencing kit (Perkin-Elmer Corp., Norwalk, Conn.) and a ABI Model 373A DNA Sequencer (Applied Biosystems, Foster City, Calif.). Nucleotide sequence was determined initially by subcloning and subsequently by using primers designed based on sequence information obtained from subcloned DNA fragments. The GCG sequence analysis software package (Genetics Computer Group, Inc., Madison, Wis.) was used for all DNA and protein sequence comparisons. DNA and protein sequences were compared to entries in Genbank and PIR, SwissProt sequence databases.

Analytical methods: plate assays, high performance liquid chromatography (HPLC), thin layer chromatography (TLC), and liquid-liquid partitioning analyses. Atrazine or hydroxyatrazine were incorporated in solid LB or minimal medium, as described in Mandelbaum et al., *Appl. Environ. Microbiol.*, 61, 1451–1457 (1995), at a final concentration of 500 µg/ml to produce an opaque suspension of small particles in the clear agar. The degradation of atrazine or hydroxyatrazine by wild-type and recombinant bacteria was indicated by a zone of clearing surrounding colonies.

High performance liquid chromatography (HPLC) analysis was performed using a Hewlett-Packard HP 1090 Liquid Chromatograph system equipped with a photodiode array detector and interfaced to an HP 79994A Chemstation. Atrazine metabolites were resolved by using an analytical $C_{18}$ reverse-phase HPLC column (Waters, Nova-Pak, 4 µm spherical packing, 150×3.9 mm) and an acetonitrile gradient, in water, at a flow rate of 1.0 ml/minute. Linear gradients of 0–6 minutes, 10–25% acetonitrile (ACN); 6–21 minutes, 25–65% ACN; 21–23 minutes, 65–100% ACN; and 23–25 minutes 100% ACN, were used. Spectral data of the column eluent was acquired between 200–400 nm (12 nm bandwidth per channel) at a sampling frequency of 640 milliseconds. Spectra were referenced against a signal at 550 nm.

Thin layer chromatography analysis was done using pre-coated silica gel 60 F254 TLC plates (Alltech Associates, Chicago, Ill.) and developed using a chloroform:methanol-:formic acid:water (75:20:4:2 v/v) solvent system. *E. coli* strains containing pMD1, pMD2, or pMD3 and Pseudomonas sp. strain ADP were grown in LB medium supplemented with appropriate antibiotics as required. After 24 hours of growth, cells were harvested by centrifugation at 10,000×g for 10 minutes, washed twice in 0.1 M phosphate buffer (pH 7.5) and resuspended in the same buffer to an absorbance of 25 at 600 nm. Reaction mixtures consisted of 100 µl of cell suspension, 390 µl 0.1 M phosphate buffer (pH 7.5), 5 µl of unlabeled atrazine stock solution (10.59 mg/ml), and 5 µl of uniformly-labelled [$^{14}$C]-atrazine (51,524 cpm/µl). After incubation for 30 minutes at 37° C., a 40 µl aliquot of each reaction mixture was spotted onto a TLC plate. A radiolabelled hydroxyatrazine standard was prepared by mixing 8 µl of uniformly ring-labelled [$^{14}$C]-hydroxyatrazine (30,531 cpm/µl) in 492 µl phosphate buffer, pH 7.5, and a 40 µl aliquot of the standard (containing 19,500 cpm) was spotted on the TLC plate. After developing, plates were scanned using a model BAS1000 Bio-Imaging Analyzer System (Fugix Co., Japan).

Liquid-liquid partitioning analysis was done as described in Mandelbaum et al., *Appl. Environ. Microbiol.*, 61, 1451–1457 (1995), except that a 50:50 (vol/vol) mixture of ethyl acetate:n-hexane was used as the organic extractant.

Chemicals. Authentic samples of atrazine (2-chloro-4-ethylamino-6-isopropylamino-1,3,5-s-triazine), desethylatrazine (2-chloro-4-amino-6-isopropylamino-s-triazine), deisopropylatrazine (2-chloro-4-ethylamino-6-amino-s-triazine), hydroxyatrazine (2-hydroxy-4-ethylamino-6-isopropylamino-s-triazine), desethylhydroxyatrazine (2-hydroxy-4-amino-6-isopropylamino-s-triazine), desisopropylhydroxyatrazine (2-hydroxy-4-amino-6-isopropylamino-s-triazine), desethyldesisopropylatrazine (2-chloro-4,6-diamino-s-triazine), simazine (2-chloro-4,6-diethylamino-s-triazine), terbutylazine (2-chloro-4-ethylamino-6-terbutylamino-s-triazine, and melamine (2,4,6-triamino-s-triazine) were obtained from Ciba Geigy Corp., Greensboro, N.C. Ammelide (2,4-dihydroxy-6-amino-s-triazine), ammeline (2-hydroxy-4,6,-diamino-s-triazine), and cyanuric acid (1,3,5-triazine-2,4,6-triol) were obtained from Aldrich Chemical Co., Milwaukee, Wis. Radiolabelled chemicals (Table 1) were obtained from Ciba Geigy Corp., Greensboro, N.C.

TABLE 1

Chemical and physical properties of [$^{14}$C]-ring-labelled compounds used in this study.

| Compound | Specific Activity (µCi/mg) | Chemical Purity (%) | Radiolabel Purity (%) | Rf value[a] |
|---|---|---|---|---|
| Atrazine | 14.6 | 97.3 | 98.6 | 0.91 |
| Hydroxyatrazine | 44.2 | 96.7 | 98.6 | 0.52 |
| Desisopropyl-hydroxyatrazine | 22.6 | 95.8 | 92.7 | 0.23 |
| Desethyl-hydroxyatrazine | 20.9 | 96.3 | 96.2 | 0.30 |
| Ammelide | 8.6 | 99.4 | 86.1 | 0.27 |
| Ammeline | 11.1 | 99.0 | 99.9 | 0.07 |
| Cyanuric acid | 12.2 | 99.7 | 98.5 | 0.27 |

[a]Determined by TLC analysis according to procedures described in the materials and methods. Unlabelled desisopropylatrazine and desethylatrazine had Rf vales of 0.79 and 0.83, respectively.

Protein Purification. *E. coli* transformed with pMD4 was grown over night at 37° C. in eight liters of LB medium containing 25 μg/ml chloramphenicol. The culture medium was centrifuged at 10,000×g for 10 minutes at 4° C., washed in 0.85% NaCl, and the cell pellet was resuspended in 50 ml of 25 mM MOPS buffer (3-[N-morpholino]propane-sulfonic acid, pH 6.9), containing phenylmethylsulfonylfluoride (100 μg/ml). The cells were broken by three passages through a Amicon French Pressure Cell at 20,000 pounds per square inch (psi) at 4° C. Cell-free extract was obtained by centrifugation at 10,000×g for 15 minutes. The supernatant was clarified by centrifugation at 18,000×g for 60 minutes and solid $NH_4SO_4$ was added, with stirring, to a final concentration of 20% (wt/vol) at 4° C. The solution was stirred for 30 minutes at 4° C. and centrifuged at 12,000×g for 20 minutes. The precipitated material was resuspended in 50 ml of 25 mM MOPS buffer (pH 6.9), and dialyzed overnight at 4° C. against 1 liter of 25 mM MOPS buffer (pH 6.9).

The solution was loaded onto a Mono Q HR 16/10 Column (Pharmacia LKB Biotechnology, Uppsala, Sweden). The column was washed with 25 mM MOPS buffer (pH 6.9), and the protein was eluted with a 0–0.5 M KCl gradient. Protein eluting from the column was monitored at 280 nm by using a Pharmacia U.V. protein detector. Pooled fractions containing the major peak were dialyzed overnight against 1 liter 25 mM MOPS buffer (pH 6.9). The dialyzed material was assayed for atrazine degradation ability by using HPLC analysis (see above) and analyzed for purity by sodium dodecyl sulfate (SDS) polyacrylamide gel electrophoreses (Laemlii).

Protein Characterization. Protein subunit sizes were determined by SDS polyacrylamide gel electrophoresis by comparison to known standard proteins, using a Mini-Protean II gel apparatus (Biorad, Hercules, Calif.). The size of the holoenzyme was determined by gel filtration chromatography on a Superose 6 HR (1.0×30.0 cm) column, using an FPLC System (Pharmacia, Uppsala, Sweden). The protein was eluted with 25 mM MOPS buffer (pH 6.9) containing 0.1 M NaCl. Proteins with known molecular weights were used as chromatography standards. Isoelectric point determinations were done using a Pharamacia Phast-Gel System and Pharamacia IEF 3-9 media. A Pharamacia broad-range pI calibration kit was used for standards.

Amino acid analysis. The amino acid composition and N-terminal amino acid sequence of purified atzA protein was determined using a Beckman 6300 Amino Acid Analyzer.

Metal analysis. The metal content of atzA protein was determined by inductively coupled plasma emission spectroscopy.

Enzyme Kinetics. Purified AtzA protein, 50 μg/ml, was added to 500 μl of different concentrations of atrazine (23.3 μM, 43.0 μM, 93 μM, 233 μM, and 435 μM in 25 mM MOPS buffer, pH 6.9) and reactions were allowed to proceed at room temperature for 2, 5, 7, and 10 minutes. The reactions were stopped by boiling the reaction tubes at specific times, the addition of 500 μl acetonitrile and rapid freezing at −80° C. Thawed samples were centrifuged at 14,000 rpm for 10 minutes, the supernatants were filtered through a 0.2 μM filter, and placed into crimp-seal HPLC vials. HPLC analysis was done as described above. Based on HPLC data, initial rates of atrazine degradation and hydroxyatrazine formation were calculated and Michaelis Menton and Lineweaver Burke plots were constructed.

Effect of simple nitrogen sources on atrazine degradation. From experiments done with Pseudomonas species strain ADP on solid media with 500 ppm atrazine and varying concentrations of ammonium chloride, ammonium chloride concentrations as low as 0.6–1.2 mM were sufficient to inhibit visible clearing on the plates, even after 2 weeks of incubation either at 28° C. or 37° C. With similar experiments using *E. coli* DH5α (pMD1 or pMD2) clearing, atrazine degradation was observed in the presence of ammonium chloride concentrations as high as 48 mM. This value is almost 40–80 fold higher than the wild-type tolerance for ammonium chloride with concomitant atrazine degradation.

Protocol for polyclonal antibody production. On Day 1 rabbits were pre-bled and immunized by a series of subcutaneous injections (approximately 10 injection sites, each with approximately 100 μl of antigen plus adjuvant). Up to 1 milligram of antigen per rabbit was used either in Complete Freund Adjuvent or polyacrylamide as adjuvant. On Days 14 and 21 the first booster was given with up to 500 micrograms of antigen per rabbit in Incomplete Freund Adjuvent or polyacrylamide. On Days 25 and 28 the first bleed was accomplished withdrawing a small amount (5 ml) of blood from an artery or vein using a 23 6A, 1 inch butterfly needle. On Days 26–34 testing was done for the presence of antibodies. On Day 42 the second booster was given with up to 500 micrograms of antigen per rabbit in Incomplete Freunds adjuvent or polyacrylamide. On Day 49 the second bleed was completed in the same manner as the first bleed. On Days 50–55 testing was again done for the presence of antibodies. The third booster was given on Day 63 with up to 200 micrograms of antigen per rabbit in Incomplete Freunds Adjuvant or polyacrylamide. The third bleed was completed on Day 70 in the same manner as the first bleed. On Day 71 testing was done for the presence of antibodies. If the antibody titre was sufficient, on Day 72 the rabbits were anesthetized with 22–44 mg of ketamine and a cardiac puncture was performed to drain the blood. The rabbits were then euthanized with an IV injection of B euthanasia. The chests were opened to be sure the euthanasia was complete. For the blood samples mentioned above, 0.1 cc of acepromazine or topical xylene was used. The acepromazine was injected (intramuscularly) IM.

Atrazine degradation gene expressed in *Bradyrhizobium japonicum*. A cosmid clone, pMD1, which contains the 22 kb DNA region from atrazine degrading Pseudomonas strain (ADP), was successfully transferred to *Bradyrhizobium japonicum* strain USDA 123. The pMD1 was transferred from *E. coli* DH5α (pMD1) to *B. japonicum* strains USDA 123 by conjugation. This was done by using helper plasmid pRK2073 and the triparental mating procedure of Leong et al., *J. Bio. Chem*, 257, 8724–8730 (1982). This was done using a modified patch mating technique. Equal quantities of *E. coli* DH5α (pMD1), *B. japonicum* strain USDA plate and spread to the size of a nickel. The patch was incubated for 4 days at 28° C. and the resulting bacterial growth was removed from the pate, serially diluted in 0.85% NaCl plus 0.01% tween 80, and spread onto the surface of minimal AG plates (Ag without yeast extract) containing 60 μg/ml tetracycline. Plates were incubated for 2 weeks at 28° C. Colonies arising in the plates were checked for atrazine degradation activity by using the plate clearing assay. Atrazine degradation was verified by HPLC analysis. The identity of transconjugants was verified by using strain specific fluorescent antibodies prepared according to Schrnidt et al., *J. Bacteriol.*, 95, 1987–1992 (1968). *B. japonicum* strain can express the atrazine degradation genes located in the cosmid clone pMD1. *B japonicuni* strain that carries pMD1 can clear atrazine in 10 days on AG media plates containing up to 500 ppm atrazine. HPLC analysis the overnight culture broth shows that all the supplied atrazine (33 ppm) is degraded and there is no atrazine detectable in the culture broth. The control strains of *B. japonicum* strain does not carry the cosmid clone, pMD1 failed to degrade atrazine both in plates and in culture broth.

Results

Cloning of genes involved in atrazine degradation. Atrazine degradation genes from Pseudomonas sp. strain ADP were cloned and expressed in E. coli DH5α. The cloning strategy was based on the ability of wild-type and recombinant bacteria to form clearing zones surrounding colonies on atrazine-amended solid medium. Clearing of atrazine on solid nutrient media by both Pseudomonas sp. strain ADP and E. coli DH5α (pMD1, pMD2, pMD3 or pMD4) provided a convenient visual assay for atrazine degradation during the cloning and subcloning procedures. Atrazine degradation was verified by HPLC. TLC, and liquid-liquid partitioning analyses (see below).

To construct the Pseudomonas sp. strain ADP genomic library, total genomic DNA was partially digested with EcoRI, ligated to the EcoRI-digested cosmid vector pLAFR3 DNA, and packaged in vitro. The completed genomic DNA library contained 2000 colonies.

To identify the atrazine degrading clones, the entire gene library was replica-plated onto LB medium containing 500 μg/ml atrazine and 15 μg/ml tetracycline. Fourteen colonies having clearing zones were identified. All fourteen clones degraded atrazine, as determined by HPLC analysis. Cosmid DNA isolated from the fourteen colonies contained cloned DNA fragments which were approximately 22 kb in length. The fourteen clones could be subdivided into six groups on the basis of restriction enzyme digestion analysis using EcoRI. All fourteen clones, however, contained the same 8.7 kb EcoRI fragment. Thirteen of the colonies, in addition to degrading atrazine, also produced an opaque material that surrounded colonies growing on agar medium. Subsequent experiments indicated that the opaque material only was observed in E. coli clones which accumulated hydroxyatrazine. Thus, the cloudy material surrounding E. coli pMD2–pMD4 colonies was due to the deposition of hydroxyatrazine in the growth medium. The one colony that degraded atrazine without the deposition of the opaque material was selected for further analysis. The cosmid from this colony was designated pMD1 (FIG. 1).

Subcloning of pMD1. To more precisely localize the DNA region involved in the initial steps in atrazine degradation, cosmid pMD1 was digested with EcoRI and the mixture was ligated into EcoRI-digested pACYC184, as described in Mandelbaum et al., *Appl. Environ. Microbiol.*, 61, 1451–1457 (1995). An atrazine degrading subclone was identified by using the plate clearing assay. This subclone, pMD2, contained the 8.7 kb EcoRI fragment identified in pMD1 (FIG. 1). Plasmid pMD2 was further subcloned by digestion with BamHI and ClaI, followed by ligation into BamHi and ClaI-digested pACYC184. An atrazine degrading subclone, pMD3, containing a 3.3 kb BamHI/ClaI fragment, was identified by using the plate-clearing assay (FIG. 1). Plasmid pMD3 was further subcloned by digestion with AvaI, and ligated into AvaI-digested pACYC184. This strategy led to the isolation of pMD4 (FIG. 1), which contained a 1.9 kb AvaI fragment encoding atrazine degradation activity.

All the clones and subclones had clearing zones surrounding single colonies in about one week, although clearing appeared sooner in the more heavily-inoculated area of streak plates. E. coli DH5α cells containing pMD2, pMD3, and pMD4 produced a clearing phenotype on LB or minimal medium containing 500 μg/ml atrazine, but they also produced an opaque secreted product, or precipitate, in the medium surrounding colonies. No secreted material was seen with E. coli DH5α(pMD1). Of the four plasmids examined, only E. coli (pMD1) produced a clearing zone on medium containing hydroxyatrazine, suggesting that a gene or genes encoding for hydroxyatrazine metabolism were located on this large cosmid.

Hybridization analyses. To determine whether the 1.9 kb AvaI fragment, which encodes atrazine degradation activity in Pseudonionus sp. strain ADP, was also present in other atrazine-degrading microorganisms, the internal 0.6 kb ApaI/PstI fragment from pMD4 was hybridized to EcoRI-digested genomic DNA from SG1, a recently-isolated, atrazine-degrading pure culture isolate from St. Gabriel, La., and an atrazine-degrading microbial consortium described in Stucki et al., *Water Res.*, 1, 291–296 (1995). Results shown in FIG. 2 indicate that the internal 0.6 kb ApaI/PstI fragment from pMD4 hybridized to a 8.7 kb EcoRI fragment and a 1.9 kb AvaI genomic DNA fragment from Pseudomonas sp. strain ADP and that the gene probe hybridized to a 8.7 kb genomic DNA fragment in strain SG1 and to a 9.3 kb fragment in DNA from the consortium. DNA from P. cepacia G4, which does not metabolize atrazine, did not hybridize to the probe. DNA from a P. cepacia G4, an organism that does not degrade atrazine, did not hybridize to the 0.6-kb probe. These results indicated that the isolated gene region, which encodes atrazine-degradation activity, was not restricted to Psezidomonas sp. strain ADP, but was present in at least two independently obtained atrazine-degrading bacteria obtained from geographically diverse locations.

To determine if the cloned gene region encoding atrazine degradation activity was located on an indigenous plasmid, a $^{32}$P-labelled 0.6 kb ApaI/PstI fragment from pMD4 was hybridized to EcoRI- and AvaI-digested plasmid DNA from Pseudomnonas sp. strain ADP. While the Pseltdomonas strain harbored at least one large plasmid of approximately 60 kb, there was no hybridization between the probe and the plasmid DNA, suggesting that the isolated gene region is located on the chromosome or on a plasmid that could not be isolated by the method used here.

Figure 3:
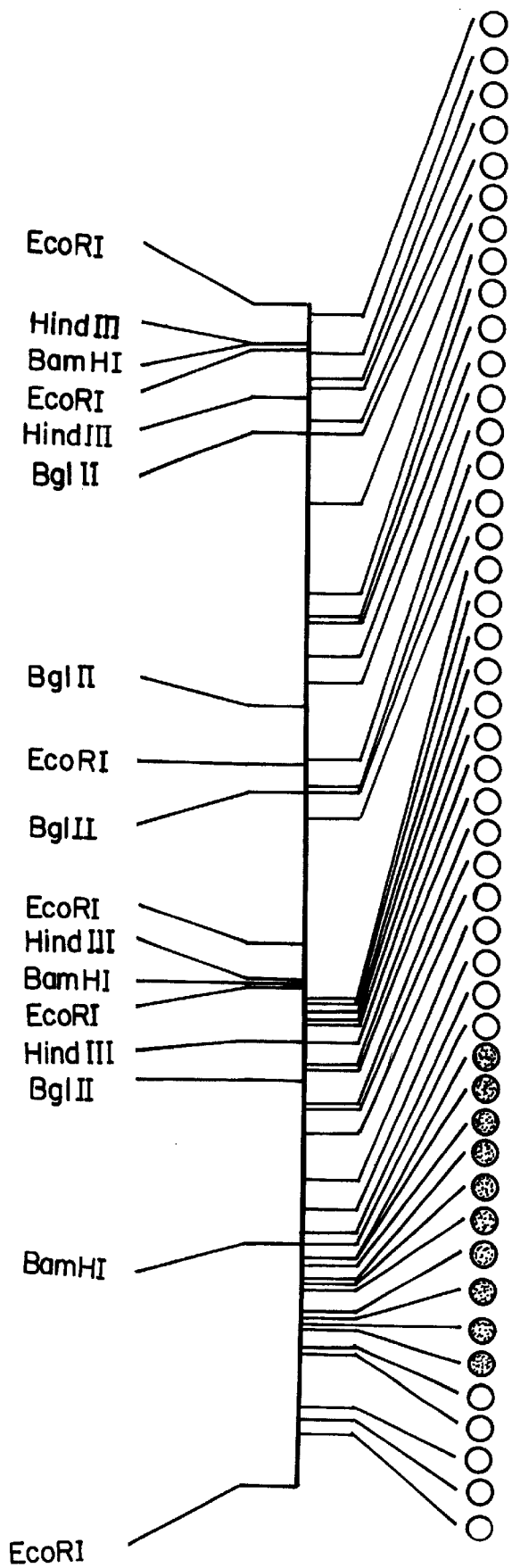
FIG. 3. Physical and genetic map of the 21.5 kb EcoRI genomic DNA fragment from Pseudomonas sp. strain ADP cloned in cosmid pMD1. Forty-six independent transposon Tn5 insertions within the cloned DNA fragment are indicated. The open and solid circles represent clearing and nonclearing phenotypes, respectively.

Tn5 mutagenesis analyses. To more precisely localize the gene region(s) involved in atrazine dechlorination and to determine if other regions of pMD1 were involved in the transformation of atrazine, random Tn5 mutagenesis in E. coli was used to generate mutations in the cloned genomic DNA fragments from Pseudomnonas sp. strain ADP. Forty-six unique Tn5 insertions in the cloned DNA were mapped using restriction enzyme digestions and Southern hybridization analysis (FIG. 3). Cosmids containing single Tn5 insertions were transformed into E. coli DH5α and the Tn5 mutants were screened for their ability to clear atrazine on solid media. All of the transposon-containing mutants that had lost the ability to clear atrazine from the growth medium mapped within the 1.9 kb AvaI fragment (i.e., the genomic DNA fragment cloned in pMD4). The Tn5 insertions in all other regions of cosmid pMD1 did not affect their ability to clear atrazine from the growth medium. Results of this mutagenesis study delimited the region essential for atrazine dechlorination to 1.3 kb and indicated that other regions of pMD1 were not required for atrazine dechlorination in E. coli.

Analysis of atrazine metabolism by E. coli clones. The extent and rate of atrazine degradation was determined in liquid culture. E. coli clones containing plasmids pMD1, pMD2, or pMD3 were compared to Pseildomonas sp. strain ADP for their ability to transform ring-labelled [$^{14}$C]-atrazine to water-soluble metabolites. This method, which measures [$^{14}$C]-label partitioning between organic and aqueous phases, had previously been used with Pseudomonas sp. ADP to show the transformation of atrazine to metabolites that partition into the aqueous phase, in Mandelbaum et al., *Appl. Environ. Microbiol.*, 61, 1451–1457 (1995). When Pseudomonas sp. strain ADP, *E. coli* (pMD1), *E. coli* (pMD2), or *E. coli* (pMD3), was incubated for 2 hours with [$^{14}$C]-atrazine, 98%, 97%, 88%, and 92%, respectively, of the total recoverable radioactivity was found in the aqueous phase (Table 2). Greater than 90% of the initial radioactivity was accounted for as atrazine plus water soluble metabolites, indicating that little or no [$^{14}$C]CO$_2$ was formed. In contrast, forty-four percent of the radioactivity was lost from the Psezidomonas ADP culture after 18.5 hours. In previous studies done with Pseltdomonas sp. strain ADP and ring-labelled $^{14}$C-atrazine, radiolabel was lost from culture filtrates as $^{14}$CO$_2$ (see, e.g., Mandelbaum et al., *Appl. Environ. Microbiol.*, 61, 1451–1457 (1995). With *E. coli* (pMD1), *E. coli* (pMD2) and *E. coli* (pMD3) cultures, essentially all the radioactivity was retained. It was found in the culture filtrate as one or more metabolites.

TABLE 2

[$^{14}$C] Atrazine transformation to water soluble metabolites by *E. coli* clones and Psendomonas sp. strain ADP.

| | [$^{14}$C]Atrazine Transformation | | | |
|---|---|---|---|---|
| | Percent Water Soluble Metabolites[a] | | Percent Recovered[b] | |
| Organism | 2 hr | 18.5 hr | 2 hr | 18.5 hr |
| Pseudomonas strain ADP | 98 | 100 | 92 | 56 |
| *E. coli* (pMD1) | 97 | 100 | 94 | 91 |
| *E. coli* (pMD2) | 88 | 97 | 96 | 92 |
| *E. coli* (pMD3) | 92 | 98 | 98 | 93 |

[a]Values equal (cpm in aqueous phase) ÷ (cpm in aqueous phase + cpm in organic phase) × 100.
[b]Values equal (cpm in aqueous phase + cpm in organic phase) ÷ (cpm of starting atrazine) × 100.

These results show that pMD1 contains genes that encode for one or more enzymes that catalyze the conversion of hydroxyatrazine to more water soluble metabolites. This data suggests that hydroxyatrazine is the first intermediate in the atrazine degradation pathway by Pseudomonas sp. strain ADP. This result is consistent with earlier studies (Mandelbaum et al., *Appl. Environ. Microbiol.*, 61, 1451–1457 (1995)) which showed that hydroxyatrazine was transiently produced during transformation of atrazine by a bacterial consortium, from which Pseudomonas sp. strain ADP was isolated (Mandelbaum et al., *Appl. Environ. Microbiol.*, 59, 1695–1701 (1993)).

To ascertain the nature of the accumulating metabolite(s), thin layer chromatography on silica gel plates was conducted. The $R_f$ values of [$^{14}$C] metabolites, obtained from culture filtrates, were compared to authentic triazine compounds that could be possible metabolites (Table 1). With *E. coli* clones containing pMD2 or pMD3, a metabolite accumulated with an $R_f$ value identical to standard hydroxyatrazine ($R_f$=0.52). The amount of radioactivity in the metabolite fraction was equivalent to the starting radioactivity of [$^{14}$C]-atrazine. A radioactive spot corresponding to the $R_f$ value of hydroxyatrazine was observed with *E. coli* (pMD1) after a few minutes of incubation. Over time, however, this spot decreased in intensity and another somewhat more polar compound ($R_f$=0.43) was observed to increase concomitantly. The Rf value of the unknown metabolite was not equivalent to any of the tested standard compounds (Table 1).

Figure 4:
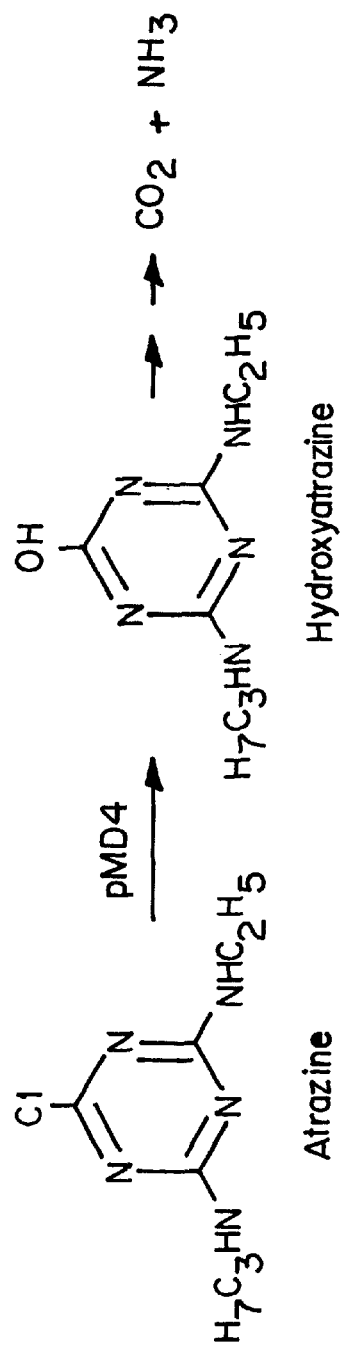
FIG. 4. Pathway for atrazine degradation in Pseudomonas sp. strain ADP. The first step is encoded by a gene region located on pMD4 and generates hydroxyatrazine, which is subsequently metabolized to carbon dioxide and ammonia.

Further evidence for the identity of the metabolite obtained from the *E. coli* clones was obtained by using HPLC analyses. Culture filtrates from *E. coli* containing pMD2, pMD3, or pMD4 contained a compound with a retention time of 6.5 minutes. This compound was not observed with the *E. coli* DH5α wild-type control. The hydroxyatrazine standard had a retention time of 6.5 minutes. Coinjection of hydroxyatrazine and culture filtrates from the recombinant strains yielded a single uniform peak. Moreover, the absorption spectrum of authentic hydroxyatrazine was identical to that obtained from the 6.5 minute peak eluting from culture filtrates. *E. coli* (pMD1) cleared atrazine from culture filtrates, but the compound eluting at 6.5 minutes was not observed even after 18 hours of incubation. HPLC analysis did not reveal another metabolite, but there was a significant amount of polar material from the growth medium that eluted between 1–4 minutes and could have obscured accumulating polar metabolites. Taken together, results of this study indicate that hydroxyatrazine is the first metabolite in the degradation of atrazine by Pseudomonas sp. strain ADP (FIG. 4).

Figure 5:
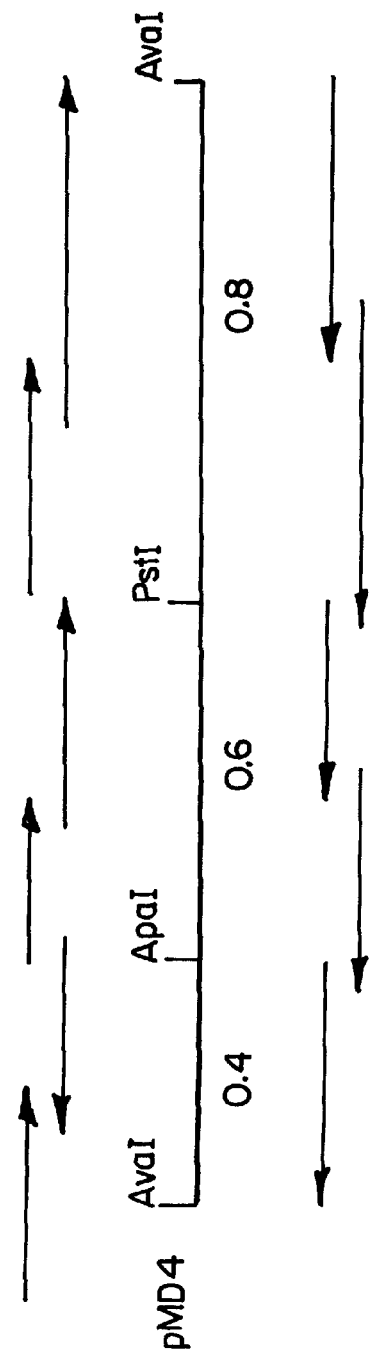
FIG. 5. Sequencing strategy for DNA fragment cloned in pMD4. Arrows indicate direction of primer sequencing reactions.

DNA and protein sequence of the atzA gene. The nucleotide sequence of the approximately 1.9-kb AvaI DNA fragment in pMD4 was determined on both strands. Nucleotide sequence was determined initially by subcloning and subsequently using primers based on sequence information obtained from subcloned DNA fragments. The sequencing strategy used is shown in FIG. 5 and the nucleotide sequence is shown in FIG. 6. DNA sequence analysis revealed several possible open reading frames (ORFs) beginning with ATG. One large ORF, beginning at base number 236 gave a translation product of 473 amino acids, was designated as the atzA gene. The atzA gene consists of 1419 nucleotides that encodes a polypeptide of 473 amino acids with an estimated M, of 52,421 and a pI of 6.6. A typical Pseitdomonas ribosome binding site, beginning with GGAGA, is located 11 bp upstream from the proposed start codon. A potential stop codon is located at position 1655.

Several lines of evidence support the conclusion that the designated ORF constitutes the atrazine chlorohydrolase gene: 1) *E. coli* transformed with pMD4, gained the ability to degrade atrazine as demonstrated by clearing zones surrounding colonies on solid media containing crystalline atrazine, 2) the dechlorination activity was abolished by transposon Tn5 insertions specifically within the 1.9-kb AvaI fragment and the Tn5 insertion was located within the ORF, 3) there is also significant homology between the atzA ORF (40.987% identity over 484 amino acid residues) and a protein from *Rhodococcus corallinus* NRRL B-15444R which possesses an analogous catalytic activity, a triazine hydrolase which is responsible for the deamination of melamine (2,4,6-triamino-1,3,5-triazine) and dechlorination of deethylsimazine. While no typical *E. coli* 10 sequence was seen preceding the predicted start of AtzA, a potential Pseudomonas ribosome binding site was found 11 base pairs upstream of the ATG (V. Shingler et al., *J. Bacteriol.*, 174, 711–724 (1992)). This is interesting given the fact that atzA was expressed in *E. coli*.

The protein sequence derived from a translation of the ORF is show in FIG. 7. N-terminal sequence analysis of AtzA indicated that the 10 amino acids detect were identical to those predicted by translating the ORF.

Homology of AtzA to other proteins. The AtzA amino acid sequence was compared to other proteins in the Swiss Prot and translated genes in Genbank/EMBL databases. The AtzA protein has the highest sequence identity, at the amino acid level, with TrzA, 40.9% (Table 3). A comparison of the sequence shows that there is a much higher degree of amino acid conservation towards the C-terminus of the proteins. Other proteins showing amino acid similarities with AtzA include: urease-alpha subunit (urea amidohydrolase), cytosine deaminase, and immidazolone-5-propionate hydrolase (IPH). The homologous proteins do not belong to any one particular group of bacteria. The AtzA protein (atrazine chlorohydrolase) is more related to TrzA and imidazolone-5-propionate hydrolase than it is to the other proteins having some amino acid similarity with atrazine chlorohydrolase. The urease proteins were tightly clustered to one another and as a group were less related to AtzA.

TABLE 3

Relationship of AtzA to other proteins at the amino acid level.

| Accession Designator | Enzyme Name | Organism | % Amino Acid Identity to AtzA |
|---|---|---|---|
| Swiss Prot Database | | | |
| P18314 | Urea Amidohydrolase | *Klebsiella aerogenes* | 20.3 |
| P16122 | Urease Alpha Subunit | *Proteus vulgaris* | 17.3 |
| P17086 | Urease Alpha Subunit | *Proteus mirabilis* | 17.1 |
| P25524 | Cytosine Deaminase | *E. coli* | 22.2 |
| P41020 | Urease Alpha Subunit | *Bacillus pasteuri* | 17.7 |
| GenBank/EMBL Database | | | |
| RERTRZA | N-ethylammeline chlorohydrolase | *Rhodococcus corallinus* | 41.0 |
| S69145 | Urease Alpha Subunit | *Rhizobium meliloti* | 22.8 |
| X63656 | Cytosine Deaminase | *E. coli* | 21.8 |
| D31856 | Imidazolone-5-proprionate hydrolase | *Bacillus subtilus* | 21.7 |

A comparison of the molecular and biochemical properties of AtzA and TrzA (Table 4) indicate that while both enzymes have a significant amount of amino acid similarity, there are major differences between these two triazine hydrolases. First, AtzA appears to only catalyze dechlorination reactions while TrzA is capable of both dechlorination and deamination reactions. Second, both enzymes have different substrate ranges and TrzA does not degrade either atrazine or simazine, both of which are environmentally important substrates for AtzA. It appears from limited substrate analysis that the substrates degraded by AtzA require a chlorine atom and an alkyamino side chain. In addition, AtzA does not degrade melamine, the primary substrate for TrzA. However, both enzymes have the ability to dechlorinate deisopropylatrazine (desethylsimazine). Taken together, these results indicate that despite amino acid similarities, both enzymes are biochemically different and catalyze significantly different reactions.

TABLE 4

Properties of triazine hydrolases from Pseudomonas sp. strain ADP and *Rhodococcus corallinus* NRRL B-1544R

| | Enzyme | |
|---|---|---|
| | N-ethylammeline chlorohydrolase (TrzA) | Atrazine chlorohydrolase (AtzA) |
| Substrate | Melamine Deethylsimazine | Atrazine |
| Products | Ammeline N-ethylammeline | Hydroxyatrazine |

TABLE 4-continued

Properties of triazine hydrolases from Pseudomonas sp. strain ADP and *Rhodococcus corallinus* NRRL B-1544R

| | Enzyme | |
|---|---|---|
| | N-ethylammeline chlorohydrolase (TrzA) | Atrazine chlorohydrolase (AtzA) |
| Reaction | Deamination and Dechlorination | Dechlorination |
| Holoenzyme | 200,000 Daltons | 240,000 Daltons |
| Subunit MW | 54 KD | ~53 KD |
| Number of subunits | 4 | 4 |

Purification of AtzA. The atrazine chlorohydrolase was purified from cell-free extracts of *E. coli* (pMD4) by precipitation with 20% (wt/vol) $NH_4SO_4$. That is, solid $NH_4SO_4$ was added to a buffered solution of the extract up to 20% of its saturation point at 4° C. The 0–20% $NH_4SO_4$ fraction was isolated and further purified by anion exchange chromatography on a Mono Q HR16/10 column. The resultant material was eluted with 0–0.5 M KCl gradient and one of the peaks was found to yield a single major band of approximately 60 kDa when subjected to SDS-PAGE.

Enzyme characterization. The molecular size of the native protein was estimated by gel filtration chromatography on a Superose 6 column to be approximately 240,000 daltons. These results, combined with SDS-PAGE analysis suggest that the enzyme is a homotetramer. No metals were detected in the native enzyme and the isoelectric point of the protein was 5.25 (Table 5).

TABLE 5

Molecular properties of purified AtzA.

| Property | AtzA |
|---|---|
| Subunit structure | $(\alpha)_4$ |
| Subunit molecular mass (kDa) | |
| SDS-Page | 60 |
| Calculated (aa quantification) | 52.42 |
| Native molecular mass (kDa) | |
| Gel filtration | 240–250 |
| Calculated (aa quantification) | 210 |
| Metal content | None detected |
| pI | |
| Observed | 5.25 |
| Calculated (aa quantification) | 6.6 |

The AtzA protein was examined for its ability to degrade various triazine compounds in vitro. Results in Table 6 show that only substrates containing a chlorine atom and an alkyamino side chain were degraded. Melamine and tertbutylazine were not substrates for AtzA.

TABLE 6

Substrate range of Atrazine chlorohydrolase (AtzA) from Pseudomonas sp. strain ADP[a].

| Substrate | |
|---|---|
| Degraded | Not Degraded |
| Atrazine | Desethyldesisopropylatrazine |
| Desethylatrazine | Melamine |

TABLE 6-continued

Substrate range of Atrazine chlorohydrolase (AtzA) from Pseudomonas sp. strain ADP[a].

Substrate

| Degraded | Not Degraded |
|---|---|
| Desisopropylatrazine | Tertbutylazine |
| Simazine | |

[a]Degradation of substrates determined by using purified enzyme in vitro.

Enzyme Kinetics. Using several concentrations of atrazine, the $K_m$ of AtzA for atrazine was estimated to be approximately 125 $\mu$M (FIG. 8). This value is slightly higher than those reported for the related triazine hydrolase TrzA which had a $K_m$ value of 82 $\mu$M for desethylsimazine and 61 $\mu$M for desethyl-s-triazine.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An isolated and purified DNA molecule encoding atrazine chlorohydrolase; the DNA molecule hybridizes to DNA complementary to DNA having the sequence shown in FIG. 6 (SEQ ID NO:1), beginning at position 236 and ending at position 1655, under the stringency conditions of hybridization in buffer containing 0.25 M $Na_2HPO_4$, 7% SDS, 1% BSA, 1.0 mM EDTA at 65° C., followed by washing with 0.1% SDS and 0.1×SSC at 65° C.

2. The isolated and purified DNA molecule of claim 1 encoding the atrazine chlorohydrolase having an amino acid sequence shown in FIG. 7 (SEQ ID NO:2).

3. The isolated and purified DNA molecule of claim 1 having the nucleotide sequence shown in FIG. 6 (SEQ ID NO:1) beginning at position 236 and ending at position 1655.

4. The isolated and purified DNA molecule of claim 1 having the nucleotide sequence shown in FIG. 6 (SEQ. ID NO: 1).

5. A vector comprising the DNA molecule of claim 1.

6. The vector of claim 5 wherein the DNA molecule of claim 1 is derived from a Pseudomonas strain.

7. A non-Pseudomonas bacterial cell comprising the vector of claim 6.

8. A method for the degradation of compounds having the following general formula:

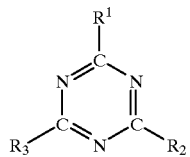

wherein $R^1$=Cl, $R^2$=$NR^4R^5$ (wherein $R^4$ and $R^5$ are each independently H or a $C_{1-3}$ alkyl group), and $R^3$=$NR^6R^7$ (wherein $R^6$ and $R^7$ are each independently H or a $C_{1-3}$ alkyl group), with the proviso that at least one of $R^2$ or $R^3$ is an alkylamino group; said method comprising adding the bacterial cell of claim 7 to a sample containing said compound.

* * * * *

UNITED STATES PATENT AND TRADEMARK OFFICE
CERTIFICATE OF CORRECTION

PATENT NO. : 6,284,522 B1
DATED : September 4, 2001
INVENTOR(S) : Lawrence P. Wackett et al.

It is certified that error appears in the above-identified patent and that said Letters Patent is hereby corrected as shown below:

Title page,
Item [56], References Cited, OTHER PUBLICATIONS,
Please delete "s-Traizine" and insert -- s-Triazine -- therefor.
Please delete "At," and insert -- Atrazine, -- therefor.
Please delete "Pate" and insert -- Page -- therefor.
Please delete the second occurrence of "Table of".

Column 1,
Line 9, please delete "Grant No.94-34339-112" and insert -- Grant No. 94-34339-1122 -- therefor.

Column 10,
Line 52, please delete "Dalgamo" and insert -- Dalgarno -- therefor.

Column 13,
Line 21, please delete "subeloning" and insert -- subcloning -- therefor.
Line 22, please delete "$\lambda$:Tn5" and insert -- $\lambda$::Tn5 -- therefor.
Line 23, please delete "rex:Tn5" and insert -- rex::Tn5 -- therefor.

Column 14,
Table 1, line 65, please delete "$R_f$ vales" and insert -- $R_f$ values -- therefor.

Column 15,
Line 28, please delete "(Laemlii)" and insert -- (Laemlii) -- therefor.
Line 39, please delete "Pharamacia" and insert -- Pharmacia -- therefor.
Line 40, please delete the first occurrence of "Pharamacia" and insert -- Pharmacia -- therefor.
Line 40, please delete the second occurrence of "Pharamacia" and insert -- Pharmacia -- therefor.

Column 17,
Line 16, please delete "HPLC. TLC," and insert -- HPLC, TLC, -- therefor.

Column 18,
Line 28, please delete "Psezidomonas" and insert -- Pseudomonias -- therefor.

UNITED STATES PATENT AND TRADEMARK OFFICE
CERTIFICATE OF CORRECTION

PATENT NO.    : 6,284,522 B1
DATED         : September 4, 2001
INVENTOR(S)   : Lawrence P. Wackett et al.

It is certified that error appears in the above-identified patent and that said Letters Patent is hereby corrected as shown below:

Column 19,
Line 25, please delete "Psendomonas" and insert -- Pseudomonias -- therefor.

Signed and Sealed this

Twelfth Day of November, 2002

Attest:

Attesting Officer

JAMES E. ROGAN
Director of the United States Patent and Trademark Office